United States Patent
Martinsson et al.

(10) Patent No.: US 11,077,113 B2
(45) Date of Patent: Aug. 3, 2021

(54) 6-ARYL-4-MORPHOLIN-1-YLPYRIDONE COMPOUNDS USEFUL FOR THE TREATMENT OF CANCER AND DIABETES

(71) Applicant: Sprint Bioscience AB, Huddinge (SE)

(72) Inventors: Jessica Martinsson, Huddinge (SE); Martin Andersson, Huddinge (SE); Johan Lindström, Huddinge (SE); Rickard Forsblom, Huddinge (SE); Fredrik Rahm, Huddinge (SE); Tobias Ginman, Huddinge (SE); Jenny Viklund, Huddinge (SE)

(73) Assignee: SPRINT BIOSCIENCE AB, Huddinge (SE)

( * ) Notice: Subject to any disclaimer, the term of this patent is extended or adjusted under 35 U.S.C. 154(b) by 489 days.

(21) Appl. No.: 15/999,530

(22) PCT Filed: Feb. 17, 2017

(86) PCT No.: PCT/EP2017/053612
§ 371 (c)(1),
(2) Date: Aug. 17, 2018

(87) PCT Pub. No.: WO2017/140841
PCT Pub. Date: Aug. 24, 2017

(65) Prior Publication Data
US 2021/0128571 A1 May 6, 2021

(30) Foreign Application Priority Data
Feb. 19, 2016 (EP) .................................... 16156530

(51) Int. Cl.
| | |
|---|---|
| *A61K 31/5377* | (2006.01) |
| *A61K 31/4745* | (2006.01) |
| *A61K 33/243* | (2019.01) |
| *A61P 35/00* | (2006.01) |
| *C07D 213/74* | (2006.01) |
| *C07D 413/04* | (2006.01) |
| *C07D 413/14* | (2006.01) |
| *A61K 45/06* | (2006.01) |

(52) U.S. Cl.
CPC ...... *A61K 31/5377* (2013.01); *A61K 31/4745* (2013.01); *A61K 33/243* (2019.01); *A61K 45/06* (2013.01); *A61P 35/00* (2018.01); *C07D 213/74* (2013.01); *C07D 413/04* (2013.01); *C07D 413/14* (2013.01)

(58) Field of Classification Search
CPC ............ A61K 31/4745; A61K 31/5377; C07D 213/74; C07D 413/04; C07D 413/14
See application file for complete search history.

(56) References Cited

U.S. PATENT DOCUMENTS

2014/0275003 A1   9/2014  Barsanti et al.

FOREIGN PATENT DOCUMENTS

| WO | WO 2004/048365 A1 | 6/2004 |
| WO | WO 2010/052569 A2 | 5/2010 |
| WO | WO 2011/001113 A2 | 1/2011 |
| WO | WO 2013/190510 A2 | 12/2013 |
| WO | WO 2014/151616 A1 | 9/2014 |
| WO | WO 2015/030057 A1 | 3/2015 |
| WO | WO 2016/044662 A1 | 3/2016 |

OTHER PUBLICATIONS

Aggarwal V. et al., "Reaction of a-Ketoketene S, N-Acetals with Cyanoacetamide: A New general Method for Substituted and Fused 4-(N-Alkylamino-, N-Arylamino-, or N-Morpholino)-3-cyano-2(1H)-pyridones", Synthesis, 1982, 1982(03): 214-216, Georg Thieme Verlag—Stuttgart—New York.

Roedig et al., "Nucleophile Substitutionen am (Z)-Perchlor-1,3-butadien-1-carbonitril mit Natriumphemolat und sekundären aliphatischen Aminen", Chemische Berichte, 1982, 115(5): 1733-1738, XP055269826, DE.

*Primary Examiner* — Alicia L Otton
(74) *Attorney, Agent, or Firm* — James S. Keddie; Bozicevic, Field & Francis LLP

(57) ABSTRACT

The invention provides novel 6-aryl or 6-heteroaryl 4-morpholin-4-yl-pyhdine-2-one compounds of formula (I), pharmaceutical compositions containing such compounds, and methods for using such compounds in treatment of diseases including cancer, diabetes, inflammatory diseases, neurodegenerative disorders, cardiovascular disorders and viral infections; wherein $R^1$, $R^2$, $R^3$ and $R^4$ are as defined in the specification.

23 Claims, No Drawings

6-ARYL-4-MORPHOLIN-1-YLPYRIDONE COMPOUNDS USEFUL FOR THE TREATMENT OF CANCER AND DIABETES

CROSS-REFERENCING

This application is a § 371 national phase of International Application No. PCT/EP2017/053612, filed on Feb. 17, 2017, which claims the benefit of European Patent Application No. 16156530.4, filed on Feb. 19, 2016, which applications are incorporated by reference herein.

FIELD OF THE INVENTION

The invention provides novel 6-aryl or 6-heteroaryl 4-morpholin-4-yl-pyridine-2-one compounds of formula (I), to pharmaceutical compositions containing such compounds, and to methods for using such compounds in treatment of diseases including cancer and diabetes.

BACKGROUND OF THE INVENTION

Enzymes belonging to the family of phosphatidylinositide 3-kinases (PI3K) are regulators of several important cellular events. The family consists of three classes, I, II and III and while the Class I group has been an interesting drug target for many years, Class II and III are less exploited.

The PI3K Class III, vacuolar protein sorting 34 (Vps34, PIK3C3) forms a heterodimer with its regulatory subunit p150 (Vps15) and this dimer takes part in several complexes regulating vesicular trafficking events such as autophagy, endocytosis, exocytosis and micropinocytosis (Amaravadi et al. Clin Cancer Res. 2011, 17:654-666; Carpentier et al. 2013, Traffic). The enzyme is responsible for phosphorylation of phosphatidylinositol (PI) to phosphatidylinositol (3)-phosphate (PI3P). The ligand binding to PX and FYVE domains results in recruiting and delocalization of these effector proteins that lead to vesicular formation, elongation and movement (Backer et al. J Biochem. 2008, 410:1-17).

Autophagy is a catabolic process where cellular components are targeted for degradation by enclosing them in double-membrane vesicles, autophagosomes that are fused with the protease-containing lysosomes. This is a means for the cell to handle damaged organelles and misfolded proteins and by that maintain cellular function. The pathway is also a way of recirculating cellular content into new building blocks (Boya et al, Nat Cell Biol 2013, 15; 713-720). Autophagy is a cellular response to stressful conditions as nutrient deprivation, acidosis and hypoxia but also to drug treatment. Therefore, autophagy inhibition is a means to potentiate cancer drugs and resensitize drug resistant tumors (Nagelkerke et al, Semin Cancer Biol 2014, 31; 99-105). Most advanced tumors show a high upregulation of autophagic flux (Leone et al. Trends in Endocrin Metab 2013, 24; 209-217). An established marker for studying autophagic flux is the detection of autophagic puncta in the form of lipidated LC3 protein on the autophagosome. Inhibition of Vps34 results in the inhibition of autophagy as measured by LC3 redistribution into puncta (Dowdle et al., Nat Cell Biol 2014, 16; 1069-79).

As recently described, ablation of the regulatory subunit p150 leads to increased insulin sensitivity in vivo due to decreased insulin receptor internalization (Nemazanyy, Nature Commun., 2015, 6:8283). A kinase dead heterozygous animal model confirms this result with increased glucose tolerance and increased insulin sensitivity (WO2013076501).

Several disease states could benefit from Vps34 inhibition including cancer, inflammatory diseases, neurodegenerative disorders, cardiovascular disorders, diabetes and viral infections (Rubinsztein et al, Nat Rev 2012, 11; 709-730). Cancer forms that would benefit from Vps34 inhibition include, but are not limited to, triple negative breast cancer, pancreas cancer, leukemia, melanoma and lung cancer. There is thus a need for novel and potent inhibitors of Vps34.

Previous disclosures describing Vps34 inhibitors in use to affect diseases include WO2015150555; WO2015150557; WO2015108861; WO2015108881; WO2012085815; WO2012085244; WO2013190510; Farkas, J. Biol. Chem., 2011 286(45)38904-12.

DESCRIPTION OF THE INVENTION

An object of the invention is to provide novel and potent inhibitors of Vps34. Another object of the invention is to provide novel and potent inhibitors of Vps34 that may be used for treating cancer and other diseases, such as diabetes.

According to one aspect of the invention, there is provided a compound of formula (I)

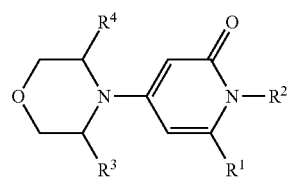

wherein
$R^1$ is aryl or heteroaryl, said aryl and said heteroaryl being mono- or bicyclic and optionally substituted with one or more of $R^5$, $R^6$, $R^7$ and $R^8$;
$R^2$, $R^3$ and $R^4$ are independently selected from hydrogen, $C_1$-$C_3$haloalkyl and $C_1$-$C_3$alkyl;
$R^5$, $R^6$, $R^7$ and $R^8$ are independently selected from halogen, $C_1$-$C_6$alkyl, $C_1$-$C_6$alkoxy, $C_1$-$C_6$haloalkyl, amino, —NHSO$_2$R$^9$, hydroxy, phenyl and a monocyclic heteroaryl;
$R^9$ is $C_1$-$C_3$haloalkyl or $C_1$-$C_3$alkyl;
and pharmaceutically acceptable salts, tautomers and stereoisomers thereof.

In one embodiment of this aspect, $R^4$ is $C_1$-$C_3$alkyl.
In one embodiment of this aspect, $R^2$ is selected from hydrogen and methyl.
In one embodiment of this aspect, $R^3$ is hydrogen.
In one embodiment of this aspect, $R^4$ is methyl.
In one embodiment of this aspect, $R^2$ is hydrogen.
In one embodiment of this aspect, $R^1$ is selected from phenyl, furyl, thienyl, pyridyl, pyrimidinyl, naphtyl, quinolinyl, indazolyl, indolyl, 4-azaindolyl, benzoxazolyl, benzimidazolyl, benzothiophenyl, each optionally substituted with one or more of $R^5$, $R^6$, $R^7$ and $R^8$.

In one embodiment of this aspect, $R^5$, $R^6$, $R^7$ and $R^8$ are independently selected from chlorine, fluorine, $C_1$-$C_3$alkyl, $C_1$-$C_3$fluoroalkyl, phenyl, amino, —NHSO$_2$CH$_3$, hydroxy, imidazolyl and pyrazolyl.

In one embodiment of this aspect, $R^1$ is selected from phenyl, furyl, thienyl, pyridyl, pyrimidinyl, naphtyl, quinolinyl, indazolyl, indolyl, 4-azaindolyl, benzoxazolyl, benzimidazolyl, benzothiophenyl, each optionally substituted with one or more of $R^5$, $R^6$, $R^7$ and $R^8$; and $R^5$, $R^6$, $R^7$ and $R^8$ are independently selected from halogen, $C_1$-$C_3$alkyl, $C_1$-$C_3$haloalkyl, phenyl, amino, —$NHSO_2CH_3$, hydroxy, imidazolyl and pyrazolyl.

In one embodiment of this aspect, $R^1$ is selected from phenyl, furyl, thienyl, pyridyl, pyrimidinyl and quinolinyl.

In one embodiment of this aspect, $R^5$ and $R^6$ are independently selected from chlorine, fluorine, trifluoromethyl, methyl, phenyl, —$NHSO_2CH_3$ and pyrazolyl.

In one embodiment of this aspect, $R^1$ is selected from phenyl, furyl, thienyl, pyridyl, pyrimidinyl and quinolinyl.

In one embodiment of this aspect, $R^1$ is selected from phenyl, furyl, thienyl, pyridyl, pyrimidinyl and quinolinyl, each optionally substituted with $R^5$ and/or $R^6$; and $R^5$ and $R^6$ are independently selected from chlorine, fluorine, trifluoromethyl, methyl, phenyl, —$NHSO_2CH_3$ and pyrazolyl.

In one embodiment of this aspect, $R^1$ is selected from

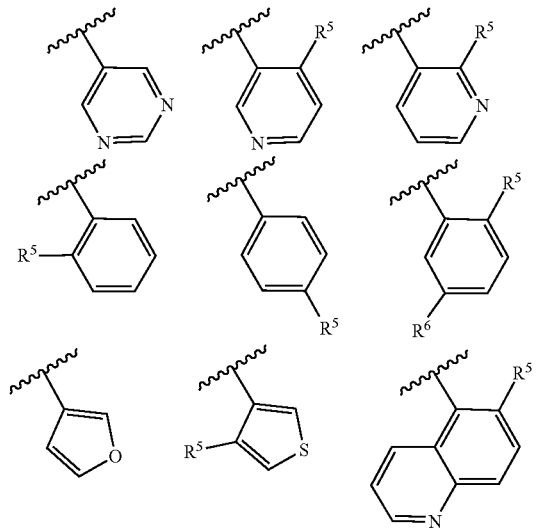

wherein $R^5$ and $R^6$ are independently selected from halogen, $C_1$-$C_3$alkyl, $C_1$-$C_3$haloalkyl, phenyl, pyrazolyl, and —$NHSO_2CH_3$.

In one embodiment of this aspect, $R^1$ is a monocyclic aryl or heteroaryl.

In one embodiment of this aspect, $R^1$ is selected from phenyl and pyridyl.

In one embodiment of this aspect, $R^5$ and $R^6$ are independently selected from chlorine, fluorine and trifluoromethyl, such as chlorine and trifluoromethyl.

In one embodiment of this aspect, $R^1$ is selected from phenyl and pyridyl, each optionally substituted with $R^5$ and/or $R^6$; and $R^5$ and $R^6$ are independently selected from chlorine, fluorine and trifluoromethyl.

In one embodiment of this aspect, $R^1$ is selected from

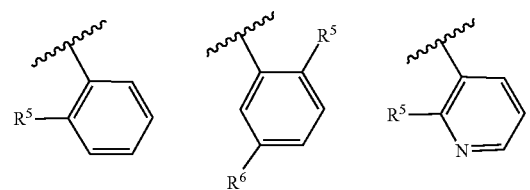

In one embodiment of this aspect, $R^1$ is selected from

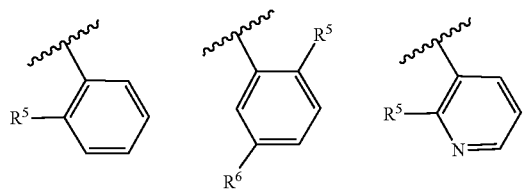

$R^4$ is $C_1$-$C_3$alkyl; and $R^5$ and $R^6$ are independently selected from chlorine, fluorine and trifluoromethyl.

In one embodiment of this aspect, $R^1$ is selected from

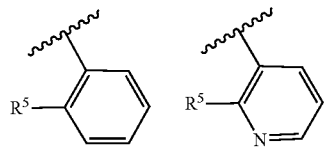

In one embodiment of this aspect, $R^1$ is selected from

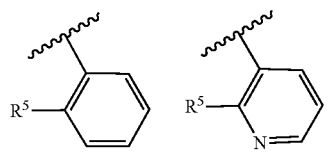

$R^2$ is hydrogen; and
$R^5$ is selected from chlorine and trifluoromethyl.

In one embodiment of this aspect, $R^1$ is selected from

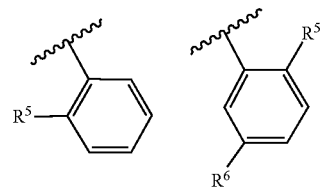

$R^2$ is hydrogen;
$R^4$ is $C_1$-$C_3$alkyl; and
$R^5$ and $R^6$ are independently selected from chlorine, fluorine and trifluoromethyl.

In one embodiment of this aspect, $R^1$ is selected from

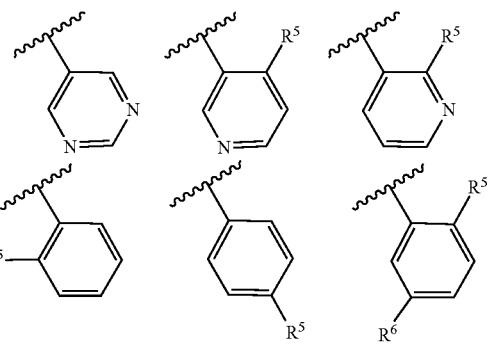

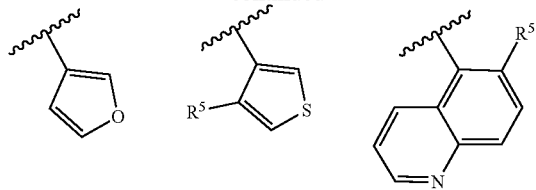

$R^2$ is hydrogen or methyl;
$R^3$ is hydrogen;
$R^4$ is methyl;
$R^5$ and $R^6$ are selected from chlorine, fluorine, trifluoromethyl, methyl, phenyl pyrazolyl and —$NHSO_2CH_3$; and pharmaceutically acceptable salts and stereoisomers thereof.

In one embodiment of this aspect, said compound is selected from:
6-(2-chlorophenyl)-4-morpholino-1H-pyridin-2-one;
6-(2-chlorophenyl)-1-methyl-4-morpholino-pyridin-2-one;
6-(2-chlorophenyl)-4-(3-methylmorpholin-4-yl)-1H-pyridin-2-one;
6-(2-chlorophenyl)-1-methyl-4-(3-methylmorpholin-4-yl)pyridin-2-one;
4-(3-methylmorpholin-4-yl)-6-(4-methyl-3-pyridyl)-1H-pyridin-2-one;
4-(3-methylmorpholin-4-yl)-6-pyrimidin-5-yl-1H-pyridin-2-one;
4-(3-methylmorpholin-4-yl)-6-(2-phenylphenyl)-1H-pyridin-2-one;
6-(2-chloro-5-fluoro-phenyl)-4-[(3R)-3-methylmorpholin-4-yl]-1H-pyridin-2-one;
4-[(3R)-3-methylmorpholin-4-yl]-6-(o-tolyl)-1H-pyridin-2-one;
4-[(3R)-3-methylmorpholin-4-yl]-6-[2-(trifluoromethyl)-3-pyridyl]-1H-pyridin-2-one;
6-(2-chlorophenyl)-4-[(3R)-3-methylmorpholin-4-yl]-1H-pyridin-2-one;
4-[(3R)-3-methylmorpholin-4-yl]-6-[2-(trifluoromethyl)phenyl]-1H-pyridin-2-one;
6-(3-furyl)-4-[(3R)-3-methylmorpholin-4-yl]-1H-pyridin-2-one;
4-[(3R)-3-methylmorpholin-4-yl]-6-(4-methyl-3-thienyl)-1H-pyridin-2-one;
N-[2-[4-[(3R)-3-methylmorpholin-4-yl]-6-oxo-1H-pyridin-2-yl]phenyl]methanesulfonamide;
4-[(3R)-3-methylmorpholin-4-yl]-6-(6-methyl-5-quinolyl)-1H-pyridin-2-one;
4-[(3R)-3-methylmorpholin-4-yl]-6-[4-(1H-pyrazol-5-yl)phenyl]-1H-pyridin-2-one; and
pharmaceutically acceptable salts, tautomers and stereoisomers thereof.

According to one aspect of the invention, there is provided a compound of formula (I)

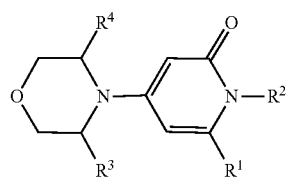

I wherein
$R^1$ is aryl or heteroaryl, said aryl and said heteroaryl being mono- or bicyclic and optionally substituted with one or more of $R^5$, $R^6$, $R^7$ and $R^8$;
$R^2$, $R^3$ and $R^4$ are independently selected from hydrogen, $C_1$-$C_3$haloalkyl and $C_1$-$C_3$alkyl;
$R^5$, $R^6$, $R^7$ and $R^8$ are independently selected from halogen, $C_1$-$C_6$alkyl, $C_1$-$C_6$alkoxy, $C_1$-$C_6$haloalkyl, amino, hydroxy, phenyl and a monocyclic heteroaryl; and
pharmaceutically acceptable salts, tautomers and stereoisomers thereof.

In one embodiment of this aspect, $R^4$ is $C_1$-$C_3$alkyl.
In one embodiment of this aspect, $R^2$ is selected from hydrogen and methyl.
In one embodiment of this aspect, $R^3$ is hydrogen.
In one embodiment of this aspect, $R^4$ is methyl.
In one embodiment of this aspect, $R^2$ is hydrogen.
In one embodiment of this aspect, $R^1$ is selected from phenyl, furyl, thienyl, pyridyl, and pyrimidinyl, naphtyl, quinolinyl, indazolyl, indolyl, 4-azaindolyl, benzoxazolyl, benzimidazolyl, benzothiophenyl, each optionally substituted with one or more of $R^5$, $R^6$, $R^7$ and $R^8$; and $R^5$, $R^6$, $R^7$ and $R^8$ are independently selected from chlorine, fluorine, methyl, trifluoromethyl, phenyl, amino, hydroxy, imidazolyl and pyrazolyl.

In one embodiment of this aspect, $R^1$ is a monocyclic aryl or heteroaryl.

In one embodiment of this aspect, wherein $R^1$ is selected from phenyl, furyl, thienyl, pyridyl, and pyrimidinyl, each optionally substituted with one or more of $R^5$ and $R^6$; and $R^5$ and $R^6$ are independently selected from chlorine, fluorine, $C_1$-$C_3$fluoroalkyl, $C_1$-$C_3$alkyl and phenyl.

In one embodiment of this aspect, $R^1$ is phenyl or 3-pyridyl, each substituted with $R^5$ and/or $R^6$.

In one embodiment of this aspect, $R^1$ is selected from

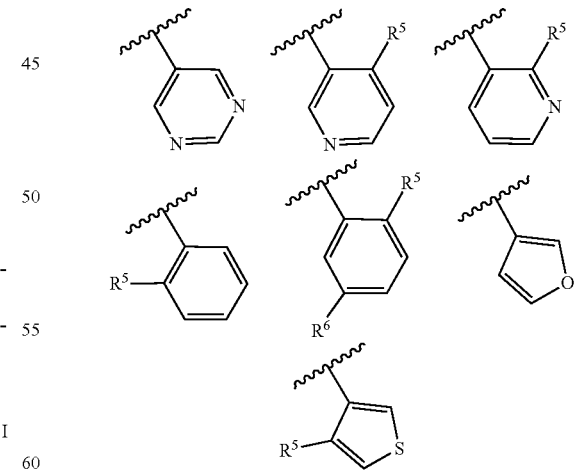

wherein $R^5$ and $R^6$ are independently selected from halogen, $C_1$-$C_3$alkyl, $C_1$-$C_3$haloalkyl and phenyl.

In one embodiment of this aspect, $R^5$ and $R^6$ are independently selected from chlorine, fluorine, trifluoromethyl and methyl.

In one embodiment of this aspect, $R^1$ is selected from

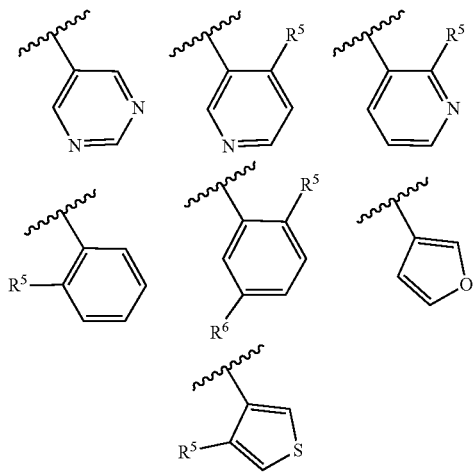

$R^2$ is hydrogen or methyl;
$R^3$ is hydrogen;
$R^4$ is hydrogen or methyl;
$R^5$ and $R^6$ are selected from chlorine, fluorine, trifluoromethyl, methyl and phenyl; and
pharmaceutically acceptable salts and stereoisomers thereof.

In one embodiment of this aspect, there is provided a compound of formula (I), said compound being selected from:
6-(2-chlorophenyl)-4-morpholino-1H-pyridin-2-one;
6-(2-chlorophenyl)-1-methyl-4-morpholino-pyridin-2-one;
6-(2-chlorophenyl)-4-(3-methylmorpholin-4-yl)-1H-pyridin-2-one;
6-(2-chlorophenyl)-1-methyl-4-(3-methylmorpholin-4-yl)pyridin-2-one;
4-(3-methylmorpholin-4-yl)-6-(4-methyl-3-pyridyl)-1H-pyridin-2-one;
4-(3-methylmorpholin-4-yl)-6-pyrimidin-5-yl-1H-pyridin-2-one;
4-(3-methylmorpholin-4-yl)-6-(2-phenylphenyl)-1H-pyridin-2-one;
6-(2-chloro-5-fluoro-phenyl)-4-[(3R)-3-methylmorpholin-4-yl]-1H-pyridin-2-one;
4-[(3R)-3-methylmorpholin-4-yl]-6-(o-tolyl)-1H-pyridin-2-one;
4-[(3R)-3-methylmorpholin-4-yl]-6-[2-(trifluoromethyl)-3-pyridyl]-1H-pyridin-2-one;
6-(2-chlorophenyl)-4-[(3R)-3-methylmorpholin-4-yl]-1H-pyridin-2-one;
4-[(3R)-3-methylmorpholin-4-yl]-6-[2-(trifluoromethyl)phenyl]-1H-pyridin-2-one;
6-(3-furyl)-4-[(3R)-3-methylmorpholin-4-yl]-1H-pyridin-2-one;
4-[(3R)-3-methylmorpholin-4-yl]-6-(4-methyl-3-thienyl)-1H-pyridin-2-one; and
pharmaceutically acceptable salts thereof.

In one aspect of the invention, there is provided a compound according to the present invention, for use in the treatment or prophylaxis of a disease.

In one aspect of the invention, there is provided a compound according to the present invention, for use in treating cancer. Typically, said cancer is selected from breast cancer, such as triple negative breast cancer, pancreas cancer, leukemia, melanoma and lung cancer.

In one aspect of the invention, there is provided a compound according to the present invention, for use in treating diabetes. Typically, said diabetes is type II diabetes.

In one aspect of the invention, there is provided a compound according to the present invention, for use in treating a disease selected from inflammatory diseases, neurodegenerative disorders, cardiovascular disorders and viral infections.

In one aspect of the invention, there is provided use of a compound according to the present invention, in the preparation of a medicament for treating cancer. Typically said cancer is selected from breast cancer, such as triple negative breast cancer, pancreas cancer, leukemia, melanoma and lung cancer.

In one aspect of the invention, there is provided use of a compound according to the present invention, in the preparation of a medicament for treating diabetes. Typically, said diabetes is type II diabetes.

In one aspect of the invention, there is provided use of a compound according to the present invention, in the preparation of a medicament for treating a disease selected from inflammatory diseases, neurodegenerative disorders, cardiovascular disorders and viral infections.

In one aspect of the invention, there is provided a method of treating cancer, comprising administering a therapeutically effective amount of a compound according to the present invention, to a patient in need thereof. Typically, said cancer is selected from breast cancer, such as triple negative breast cancer, pancreas cancer, leukemia, melanoma and lung cancer.

In one aspect of the invention, there is provided a compound according to the present invention, for use in treating cancer, wherein said cancer treatment further comprises radiation therapy.

In one aspect of the invention, there is provided a method of treating cancer, comprising administering a therapeutically effective amount of a compound according to the present invention, to a patient in need thereof, in conjunction with radiation therapy.

The compounds of the present invention may also be employed in cancer treatment in conjunction with radiation therapy and/or surgical intervention. Generally, the use of cytotoxic and/or cytostatic agents in combination with a compound or composition of the present invention will serve to:

(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

In one aspect of the invention, there is provided a method of treating diabetes, comprising administering a therapeutically effective amount of a compound according to the present invention, to a patient in need thereof. Typically, said diabetes is type II diabetes.

In one aspect of the invention, there is provided a method of treating a disease selected from inflammatory diseases, neurodegenerative disorders, cardiovascular disorders and viral infections, comprising administering a therapeutically effective amount of a compound according to the present invention, to a patient in need thereof.

In one aspect of the invention, there is provided a method of treating a disease selected from inflammatory diseases, neurodegenerative disorders, and viral infections, comprising administering a therapeutically effective amount of a compound according to the present invention, to a patient in need thereof.

In one aspect of the invention, there is provided a pharmaceutical composition comprising a compound according to the present invention, and a pharmaceutically acceptable diluent, carrier and/or excipient.

In one aspect of the invention, there is provided a pharmaceutical composition, comprising a therapeutically effective amount of a compound according to the invention and another anticancer agent selected from alkylating agents, antimetabolites, anticancer camptothecin derivatives, plan-derived anticancer agents, antibiotics, enzymes, platinum coordination complexes, tyrosine kinase inhibitors, hormones, hormone antagonists, monoclonal antibodies, interferons, and biological response modifiers.

As used herein, the term "$C_1$-$C_6$alkyl" means both linear and branched chain saturated hydrocarbon groups with 1 to 6 carbon atoms. Examples of $C_1$-$C_6$alkyl groups include methyl, ethyl, n-propyl, isopropyl, n-butyl, iso-butyl, sec-butyl, t-butyl, n-pentyl, 4-methyl-butyl, n-hexyl, 2-ethyl-butyl groups. Among unbranched $C_1$-$C_6$alkyl groups, typical ones are methyl, ethyl, n-propyl, n-butyl, n-pentyl and n-hexyl groups. Among branched alkyl groups, there may be mentioned iso-propyl, iso-butyl, sec-butyl, t-butyl, 4-methyl-butyl and 2-ethyl-butyl groups.

As used herein, the term "$C_1$-$C_3$alkyl" means both linear and branched chain saturated hydrocarbon groups with 1 to 3 carbon atoms. Examples of $C_1$-$C_3$alkyl groups include methyl, ethyl, n-propyl and isopropyl groups.

As used herein, the term "$C_1$-$C_6$alkoxy" means the group O-alkyl, where "$C_1$-$C_6$alkyl" is used as described above. Examples of $C_1$-$C_6$alkoxy groups include, but are not limited to, methoxy, ethoxy, isopropoxy, n-propoxy, n-butoxy, n-hexoxy, 3-methyl-butoxy groups.

As used herein, the term "$C_1$-$C_6$haloalkyl" means both linear and branched chain saturated hydrocarbon groups, with 1 to 6 carbon atoms and with 1 to all hydrogens substituted by a halogen of different or same type. Examples of $C_1$-$C_6$haloalkyl groups include methyl substituted with 1 to 3 halogen atoms, ethyl substituted with 1 to 5 halogen atoms, n-propyl or iso-propyl substituted with 1 to 7 halogen atoms, n-butyl or iso-butyl substituted with 1 to 9 halogen atoms, and sec-butyl or t-butyl groups substituted with 1 to 9 halogen atoms.

As used herein, the term "$C_1$-$C_3$haloalkyl" means both linear and branched chain saturated hydrocarbon groups, with 1 to 3 carbon atoms and with 1 to all hydrogens substituted by a halogen of different or same type. Examples of $C_1$-$C_3$haloalkyl groups include methyl substituted with 1 to 3 halogen atoms, ethyl substituted with 1 to 5 halogen atoms, and n-propyl or iso-propyl substituted with 1 to 7 halogen atoms.

As used herein, the term "$C_1$-$C_3$fluoroalkyl" means both linear and branched chain saturated hydrocarbon groups, with 1 to 3 carbon atoms and with 1 to all hydrogen atoms substituted by a fluorine atom. Examples of $C_1$-$C_3$fluoroalkyl groups include methyl substituted with 1 to 3 fluorine atoms, ethyl substituted with 1 to 5 fluorine atoms, and n-propyl or iso-propyl substituted with 1 to 7 fluorine atoms.

As used herein, the term "halogen" means fluorine, chlorine, bromine or iodine.

As used herein, the term "aryl" means a monocyclic or bicyclic aromatic carbocyclic group. Examples of aryl groups include phenyl and naphthyl. A naphthyl group may be attached through the 1 or the 2 position. In a bicyclic aryl, one of the rings may be partially saturated. Examples of such groups include indanyl and tetrahydronaphthyl.

As used herein, the term "monocyclic aryl" means a monocyclic aromatic carbocyclic group. Examples of monocyclic aryl groups include phenyl.

As used herein, the term "heteroaryl" means a monocyclic or bicyclic aromatic group of carbon atoms wherein from one to three of the carbon atoms is/are replaced by one or more heteroatoms independently selected from nitrogen, oxygen or sulfur. In a bicyclic heteroaryl, one of the rings may be partially saturated. Examples of such groups include indolinyl and 1,3-benzodioxolyl.

As used herein, the term "monocyclic heteroaryl" means a monocyclic aromatic group of carbon atoms wherein from one to three of the carbon atoms is/are replaced by one or more heteroatoms independently selected from nitrogen, oxygen or sulfur.

Examples of monocyclic heteroaryl groups include, but are not limited to, furyl, thienyl, pyrrolyl, oxazolyl, thiazolyl, imidazolyl, oxadiazolyl, thiadiazolyl, pyridyl, triazolyl, triazinyl, pyridazyl, isothiazolyl, isoxazolyl, pyrazinyl, pyrazolyl, and pyrimidinyl.

Examples of bicyclic heteroaryl groups include, but are not limited to quinoxalinyl, quinazolinyl, pyridopyrazinyl, benzoxazolyl, benzothiophenyl, benzimidazolyl, naphthyridinyl, quinolinyl, benzofuryl, indolyl, indazolyl, benzothiazolyl, pyridopyrimidinyl, and isoquinolinyl.

Depending on the substituents present in compounds of the formula (I), the compounds may form salts which are within the scope of the present invention. Salts of compounds of formula (I), which are suitable for use in medicine are those wherein a counterion is pharmaceutically acceptable.

Suitable salts according to the invention include those formed with organic or inorganic acids or bases. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_1$-$C_4$)alkyl or aryl sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine.

Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucamine, morpholine, thiomorpholine, piperidine, pyrrolidine, a mono, dior tri lower alkylamine, for example ethyl, tertbutyl, diethyl, diisopropyl, triethyl, tributyl or dimethylpropylamine, or a mono-, di- or trihydroxy lower alkylamine, for example mono-, di- or triethanolamine. Corresponding internal salts may furthermore be formed.

The compounds of the invention may be used in the prophylaxis and/or treatment as such, or in a form of a pharmaceutical composition. While it is possible for the active ingredient to be administered alone, it is also possible for it to be present in a pharmaceutical composition. Accordingly, the invention provides a pharmaceutical composition comprising a compound of formula (I), and a pharmaceutically acceptable diluent, excipient and/or carrier. Pharmaceutical compositions of the invention may take the form of a pharmaceutical formulation as described below.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate, calcium sulfate, sorbitol, glucose and/or lactose and/or other excipients, binders, extenders, disintegrants, diluents and lubricants such as those known in the art. Suitable binders include starch, gelatin, natural sugars such as glucose or beta-lactose, corn sweeteners, natural and synthetic gums such as acacia, tragacanth or sodium alginate, carboxymethylcellulose, poly-ethylene glycol, waxes and the like. Disintegrators include without limitation starch, methylcellulose, agar, bentonite, xanthan gum and the like. The compounds of formula (I) can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use. Lubricants used in these dosage forms include sodium oleate, sodium stearate, magnesium stearate, sodium benzoate, sodium acetate, sodium chloride and the like. For oral administration in liquid form, the oral drug components can be combined with any oral, non-toxic, pharmaceutically acceptable inert carrier such as ethanol, glycerol, water, and the like.

Compositions of the present invention suitable for oral administration may be presented as discrete units such as capsules, cachets, pills or tablets each containing a predetermined amount of the active ingredient; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Typical unit dosage compositions are those containing an effective dose, as hereinbefore recited, or an appropriate fraction thereof, of the active ingredient.

It should be understood that in addition to the ingredients particularly mentioned above, the compositions of this invention may include other agents conventional in the art having regard to the type of formulation in question, for example those suitable for oral administration may include flavoring agents.

The compositions may be presented in unit dosage form and may be prepared by any of the methods well known in the art of pharmacy. Methods may include the step of bringing the active ingredient into association with the carrier which constitutes one or more accessory ingredients. Compositions may be prepared by uniformly and intimately bringing into association the active ingredient with liquid carriers or finely divided solid carriers or both and then, if necessary, shaping the product into the desired formulation.

The compounds of the present invention can also be administered in the form of liposome delivery systems, such as small unilamellar vesicles, large unilamellar vesicles and multilamellar vesicles. Liposomes can be formed from a variety of phospholipids, 1,2-dipalmitoylphosphatidylcholine, phosphatidyl ethanolamine (cephaline), phosphatidylserine, phosphatidylinositol, diphosphatidylglycerol (cardiolipin) or phosphatidylcholine (lecithin).

Compositions for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as polyethylene glycol, ethanol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Compositions for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Compositions for topical administration in the mouth, for example buccally or sublingually, include lozenges comprising the active ingredient in a flavored basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Compounds of formula (I) may be administered as the sole pharmaceutical agent or in combination with one or more additional therapeutic agents where the combination causes no unacceptable adverse effects. This pharmaceutical composition includes administration of a single pharmaceutical dosage formulation which contains a compound of formula (I) and one or more additional therapeutic agents, as well as administration of the compound of formula (I) and each additional therapeutic agent in its own separate pharmaceutical dosage formulation. For example, a compound of formula (I) and a therapeutic agent may be administered to the patient together in a single oral dosage composition such as a capsule or tablet, or each agent may be administered in formulations with separate dosage.

Where separate dosage compositions are used, the compound of formula (I) and one or more additional therapeutic agents may be administered at essentially the same time (e.g., concurrently) or at separately staggered times (e.g., sequentially).

The amount of active ingredient which is required to achieve a therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day, for adult humans. For oral administration, the compositions may be provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated. A medicament typically contains from about 0.01 mg to about 500 mg of the active ingredient, preferably from about 1 mg to about 100 mg of active ingredient. Intravenously, the most preferred doses will range from about 0.1 to about 10 mg/kg/minute during a constant rate infusion. Compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

EXAMPLES

Below follows a number of non-limiting examples of the invention.

The following table lists the abbreviations used in this section.

Abbreviations Meaning

Amphos (4-(N,N-Dimethylamino)phenyl)di-tert-butyl phosphine
anh. anhydrous
aq. aqueous
BuLi butyl lithium
DCM dichloromethane
DMAc N,N-dimethylacetamide
DMF N,N-dimethyl formamide
DMSO dimethyl sulfoxide
DTT Dithiothreitol
EtOAc ethyl acetate
EtOH ethanol
h hour(s)
HPLC high pressure (or performance) liquid chromatography
KOtBu potassium tert-butoxide
LCMS liquid chromatography mass spectrometry
MeCN acetonitrile
2-MeTHF 2-methyltetrahydrofuran
MeOH methanol
MIDA N-methyliminodiaceticacid
min. minute(s)
NMR nuclear magnetic resonance
Pd(OAc)$_2$ palladium(II) acetate
quant. quantitative
rt room temperature
sat. saturated
TFA trifluoroacetic acid
THF tetrahydrofuran
TLC thin layer chromatography
Preparation of Compounds Scheme 1 and 2 described below illustrate general synthetic routes to compounds of formula (I) of the invention but are not intended to be limiting. The compounds in the present invention may be prepared as a free base or a pharmaceutically acceptable salt thereof. Throughout the following description of such processes it is understood that, where appropriate, suitable protecting groups will be added to, and subsequently removed from the various reactants and intermediates in a manner that will be readily understood by one skilled in the art of organic synthesis. Conventional procedures for using such protecting groups as well as examples of suitable protecting groups are for example described in *Protective Groups in Organic Synthesis* by T. W. Greene, P. G. M Wutz, 4$^{th}$ Edition, Wiley-Interscience, New York, 2006. It is to be understood that microwaves can alternatively be used for the heating of reaction mixtures.

$R^1$, $R^2$, $R^3$, $R^4R^5$, $R^6$, $R^7$, $R^8$ and $R^9$ are, unless specified otherwise, as defined in formula (I).

(i) Formation of the Corresponding Compound of Formula (III)

A compound of formula (III) may be obtained (Scheme 1) by starting from, for example, a compound of formula (II), wherein LG represents a leaving group such as halogen (e.g. chlorine, bromine or iodine), or an alkyl-, aryl- or haloalkyl-sulfonate (such as triflate), and reacting said compound (II) with a compound of formula T-R$^1$, wherein R$^1$ is defined as above and T represents a boronic acid, a boronic ester or a potassium trifluoroborate or a MIDA boronate or a stannane, under the influence of a transition metal catalyst as described in for example *Metal-Catalyzed Cross-Coupling Reactions, 2$^{nd}$, Completely Revised and Enlarged Edition* by A. de Meijere and F. Diederich, Wiley VCH, 2004. The compound of formula T-R$^1$ may be generated from the corresponding LG-R, wherein LG represents a leaving group such as halogen (e.g chlorine, bromine or iodine) by known methods as described in for example *Advanced Organic Chemistry, Part A and B* by F. A. Carey and R. J. Sundberg, 5$^{th}$ edition, Springer Science, 2007.

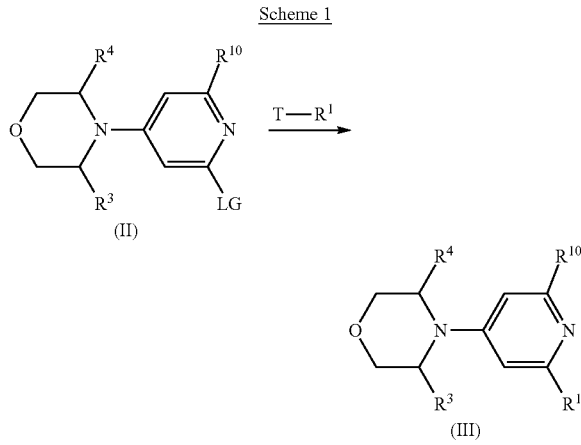

The reaction may be carried out by coupling of a compound of formula (II), with an appropriate aryl or heteroaryl boronic acid or boronic ester or stannane of formula T-R$^1$. The reaction may be carried out using a suitable metal catalyst such as palladium catalyst, such as di-tert-butylphosphinoferrocene palladium (II) dichloride, tetrakis(triphenylphosphine)palladium (0), palladium diphenylphosphinoferrocene dichloride, palladium(II) acetate or bis(dibenzylideneacetone) palladium (0). Optionally a suitable ligand such as triphenylphosphine, tri-tert-butylphosphine or 2-(dicyclohexylphosphino)biphenyl is employed in the coupling reaction. In addition, a suitable base, such as cesium fluoride, an alkyl amine, such as triethyl amine, or an alkali metal or alkaline earth metal carbonate or hydroxide or phosphate such as potassium carbonate, sodium carbonate, cesium carbonate, or sodium hydroxide, or potassium phosphate, may be used in the reaction. Said reaction may be performed at a temperature in the range between +20° C. and +160° C., in a suitable solvent, such as toluene, tetrahydrofuran, 2-methyl-tetrahydrofuran, 1,4-dioxane, dimethoxyethane, acetonitrile, water, ethanol, N,N-dimethylacetamide or N,N-dimethylformamide, or mixtures thereof. If enantiomerically pure or enriched compound (II) is used in this reaction, an enantiomerically pure or enantiomerically enriched compound (III) is obtained.

(ii) Formation of a Corresponding Compound of Formula (I)

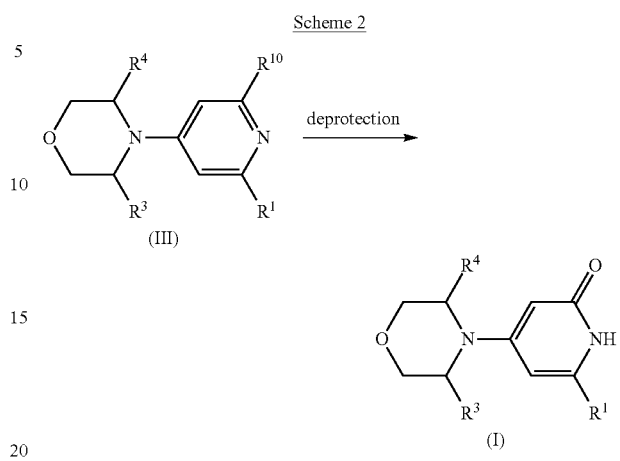

A compound of formula (I) may be obtained (Scheme 2) by starting from, for example, a compound of formula (III), wherein R$^{10}$ may be F, OCH$_3$, OC(CH$_3$)$_3$, or OSiR'R"R'" (wherein R', R" and R'" are independently aryl (such as phenyl) or alkyl (such as methyl or tert-butyl)). If R$^{10}$ is F the conversion into (I) may be carried out by for instance acidic hydrolysis using aq. HCl. If R$^{10}$ is OCH$_3$ the conversion into (I) may be carried out by reaction with for instance TMSI in a suitable solvent such as chloroform or by reaction with HBr in a suitable solvent such as acetic acid or by reaction with BBr$_3$ in a suitable solvent such as DCM. If R$^{10}$ is OC(CH$_3$)$_3$ the conversion into (I) may be carried out by reaction with for instance trifluoroacetic acid in a suitable solvent such as dichloromethane. If R$^{10}$ is OSiR'R"R'" the conversion into (I) may be carried out by for instance HCl in a suitable solvent such as methanol or by using tetrabutyl ammonium fluoride in tetrahydrofuran. If enantiomerically pure or enriched compound (III) is used in this reaction, an enantiomerically pure or enantiomerically enriched compound (I) is obtained.

Compounds of formula (II), (II) and T-R$^1$ are commercially available compounds, or are known in the literature, or they are prepared by standard processes known in the art. A compound of formula (I), (II) or (III) may be separated into its enantiomers by standard processes known in the art by for example chromatography on a chiral stationary phase.

General Methods

All solvents used were of analytical grade and commercially available anhydrous solvents were routinely used for reactions. Starting materials were available from commercial sources, or prepared according to literature procedures. Room temperature refers to +20-25° C. Solvent mixture compositions are given as volume percentages or volume ratios. Microwave heating was performed in a Biotage Initiator microwave cavity producing continuous irradiation at 2.45 GHz. It is understood that microwaves may be used for the heating of reaction mixtures. Straight phase chromatography was manually performed on Merck Silica gel 60 (0.040-0.063 mm), or automatically using an ISCO Combiflash® Companion™ system using SiliaSep™ normal-phase flash columns using the solvent system indicated.

NMR spectra were recorded on a 400 MHz (or higher field) NMR spectrometer fitted with a probe of suitable configuration. Spectra were recorded at ambient temperature unless otherwise stated. NMR spectra were acquired in CDCl$_3$, DMSO-d$_6$ or CD$_3$OD. Chemical shifts are given in ppm down- and upfield from TMS (0.00 ppm). The following reference signals were used: the residual solvent signal of DMSO-$d_5$ δ 52.5 or the residual solvent signal of CHCl$_3$ δ 7.26. Resonance multiplicities are denoted s, d, t, q, m and br for singlet, doublet, triplet, quartet, multiplet and broad, respectively.

High pressure liquid chromatography (HPLC) was performed on a reverse phase column. A linear gradient was applied using for example mobile phase A (aqueous 0.1% NH$_3$ or aqueous 0.1% acetic acid or aqueous 0.1% formic acid) and B (acetonitrile or methanol). Mass spectrometer (MS) analyses were performed in positive ion mode using electrospray ionization (ES+).

Preparative chromatography was run on a Gilson-PREP GX271 or GX281 with Trilution Ic as software on a reverse phase column. A linear gradient was applied using for example mobile phase A (aqueous 0.1% NH$_3$ or aqueous 0.1% acetic acid or aqueous 0.1% formic acid) and B (acetonitrile or methanol).

Preparative chiral chromatography for separation of enantiomers was run on a Thar SFC using supercritical fluid chromatography on a chiral stationary phase. A linear gradient was applied using mobile phase A (carbon dioxide) and B (acetonitrile or methanol or ethanol or 2-propanol or any mixtures thereof). Additives (such as diethyl amine or isopropyl amine or ammonia or formic acid or TFA) may be used.

Compounds have been named using Accelrys Draw 4.1 SP1.

Intermediate Example 1

6-(2-chlorophenyl)-4-hydroxy-1H-pyridin-2-one

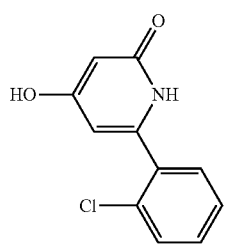 [SMILES: O=c1cc(O)cc(-c2ccccc2Cl)[nH]1]

Ethyl 3-oxobutanoate (6.33 ml, 50 mmol) was added dropwise to a suspension of NaH (60%, 1.92 g, 50 mmol) in 2-MeTHF (60 ml) at −78° C. under a nitrogen atmosphere. After 5 min the cooling bath was removed and the mixture was stirred at rt for 20 min. The mixture was cooled back to −78° C. and 1.6 M n-BuLi (31.25 ml) was added slowly over 20 min. The resulting solution was stirred at −78° C. for 30 min. Then 2-chlorobenzonitrile (6.88 g, 50 mmol) was added as a solid in one portion and the reaction mixture was stirred on the thawing cooling bath overnight. The mixture was cooled to 0° C. and MeOH (15 ml) was added slowly. The cooling bath was removed and the mixture was stirred at rt for 30 min and then cooled to 0° C. again. The mixture was neutralized by slow addition of conc. HCl and the resulting precipitate was filtered off, washed with EtOH, Pentane and dried to give the product as a solid (11.08 g, 87%). MS ES+ m/z 222 [M+H]$^+$.

Intermediate Example 2

2,4-dichloro-6-(2-chlorophenyl)pyridine

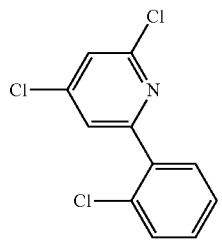 [SMILES: Clc1cc(Cl)nc(-c2ccccc2Cl)c1]

6-(2-chlorophenyl)-4-hydroxy-1H-pyridin-2-one (5 g, 22.56 mmol) was taken up in POCl$_3$ (40 ml) and N,N-dimethylaniline (5.5 ml, 43.4 mmol) was added slowly. The resulting mixture was refluxed overnight. When cooled to rt the mixture was poured onto ice (600 ml) and stirred at rt for 30 min. The precipitate was filtered off and washed with water. The solid was dissolved in EtOAc (100 ml), dried over Na$_2$SO$_4$, filtered and concentrated to give the product as a solid (7 g, 83%). MS ES+ m/z 258 [M+H]$^+$.

Intermediate Example 3

4-chloro-6-(2-chlorophenyl)-1H-pyridin-2-one

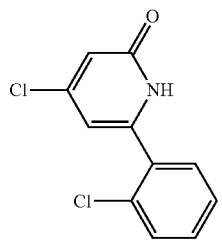 [SMILES: O=c1cc(Cl)cc(-c2ccccc2Cl)[nH]1]

2,4-dichloro-6-(2-chlorophenyl)pyridine (5.7 g, 22.05 mmol) and KOtBu (6.19 g, 55.12 mmol) were taken up in Toluene (75 ml) and the resulting mixture was stirred at 100° C. for 2 h. When cooled to rt, water (40 ml) was added and the organic layer separated. The aqueous layer was made slightly acidic using conc. HCl and extracted with EtOAc (2×40 ml). The combined organics were washed with brine (50 ml), dried over Na$_2$SO$_4$, filtered and concentrated. The resulting residue was taken up in DCM (30 ml) and TFA (5 ml, 67.3 mmol) was added. The reaction mixture was stirred at rt for 1 h, concentrated and the resulting residue was taken up in MeOH (25 ml). 30% NH$_4$OH (20 ml) and water (20 ml) were added and the mixture was stirred at rt overnight. The formed precipitate was filtered off, washed with water, EtOH, Pentane and dried to give the product as a solid (4.13 g, 78%). MS ES+ m/z 240 [M+H]$^+$.

Example 1

6-(2-chlorophenyl)-4-morpholino-1H-pyridin-2-one

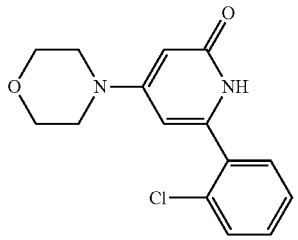 [SMILES: O=c1cc(N2CCOCC2)cc(-c2ccccc2Cl)[nH]1]

4-chloro-6-(2-chlorophenyl)-1H-pyridin-2-one (80 mg, 0.33 mmol) was taken up in morpholine (1 ml, 11.56 mmol) and the resulting mixture was stirred at 120° C. for 2 h. When cooled to rt water (5 ml) and EtOAc (5 ml) were added. The organic layer was separated and the aqueous layer was extracted with EtOAc (2×5 ml). The combined organics were dried over $Na_2SO_4$, filtered and concentrated. The resulting residue was taken up in 2-propanol (2 ml) and Heptane (8 ml) was added. The mixture was stirred at rt overnight and a precipitate was filtered off and discarded. The filtrate was concentrated and taken up in DCM (2 ml) and Heptane (8 ml) was added. After stirring at rt for 10 min the resulting precipitate was filtered off and dried to give the product as a solid (48 mg, 49%). $^1$H NMR (400 MHz, DMSO-$d_6$) δ 11.06 (br s, 1H), 7.61-7.52 (m, 1H), 7.52-7.32 (m, 3H), 6.06 (s, 1H), 5.47 (s, 1H), 3.65 (s, 4H), 3.24 (s, 4H). MS ES+ m/z 291 [M+H]$^+$.

Example 2

6-(2-chlorophenyl)-1-methyl-4-morpholino-pyridin-2-one

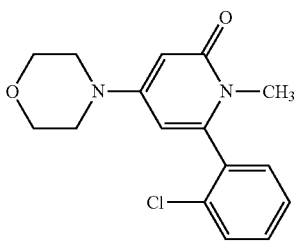 [SMILES: Cn1c(-c2ccccc2Cl)cc(N2CCOCC2)cc1=O]

6-(2-chlorophenyl)-4-morpholino-1H-pyridin-2-one (100 mg, 0.34 mmol) and $K_2CO_3$ (71.3 mg, 0.52 mmol) were taken up in MeCN (2 ml) at rt and iodomethane (0.03 ml, 0.52 mmol) was added. The resulting mixture was stirred at rt overnight. More iodomethane (0.1 ml) was added and the mixture was stirred at 70° C. overnight. When cooled to rt the mixture was filtered and purified by preparative HPLC to give the product as a solid (46 mg, 44%). $^1$H NMR (500 MHz, DMSO-$d_6$) δ 7.65-7.61 (m, 1H), 7.57-7.52 (m, 1H), 7.51-7.47 (m, 2H), 6.05 (d, 1H), 5.61 (d, 1H), 3.64 (t, 4H), 3.27-3.18 (m, 4H), 2.98 (s, 3H). MS ES+ m/z 305 [M+H]$^+$.

Example 3

6-(2-chlorophenyl)-4-(3-methylmorpholin-4-yl)-1H-pyridin-2-one

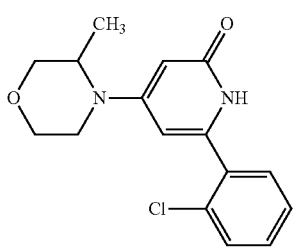 [SMILES: CC1COCCN1c1cc(-c2ccccc2Cl)[nH]c(=O)c1]

4-chloro-6-(2-chlorophenyl)-1H-pyridin-2-one (65 mg, 0.27 mmol) and 3-methylmorpholine (0.15 ml, 1.32 mmol) were mixed and heated in a microwave reactor at 160° C. for 30 min. Heated again at 180° C. for 1 h. Heated again at 200° C. for 1 h. When cooled to rt the mixture was dissolved in MeOH, filtered and purified by preparative HPLC to give the product as a solid (44 mg, 53%). $^1$H NMR (400 MHz, DMSO-$d_6$) δ 7.55 (d, 1H), 7.51-7.38 (m, 3H), 6.02 (s, 1H), 5.40 (s, 1H), 3.98-3.83 (m, 2H), 3.69-3.54 (m, 2H), 3.46 (t, 1H), 3.41-3.35 (m, 1H), 3.10-2.95 (m, 1H), 1.11 (d, 3H). MS ES+ m/z 305 [M+H]$^+$.

Example 4

6-(2-chlorophenyl)-1-methyl-4-(3-methylmorpholin-4-yl)pyridin-2-one

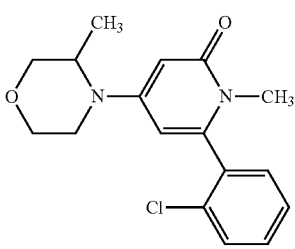 [SMILES: CC1COCCN1c1cc(-c2ccccc2Cl)n(C)c(=O)c1]

6-(2-chlorophenyl)-4-(3-methylmorpholin-4-yl)-1H-pyridin-2-one (75 mg, 0.25 mmol) and $K_2CO_3$ (50 mg, 0.36 mmol) were taken up in MeCN (1 ml). Iodomethane (0.02 ml, 0.32 mmol) was added and the mixture was stirred at rt for 30 min. DMAc (0.5 ml) was added and the mixture was stirred at rt overnight. MeOH (1 ml) and Iodomethane (0.05 ml, 0.8 mmol) were added and stirring continued at rt overnight. The mixture was filtered and purified by preparative HPLC to give the product as a solid (46 mg, 59%). $^1$H NMR (500 MHz, DMSO-$d_6$) 7.63 (d, 1H), 7.57-7.48 (m, 3H), 6.01 (t, 1H), 5.58-5.53 (m, 1H), 4.00-3.84 (m, 2H), 3.70-3.56 (m, 2H), 3.50-3.34 (m, 2H), 3.04-2.97 (m, 4H), 1.10 (t, 3H). MS ES+ m/z 319 [M+H]$^+$.

Intermediate Example 4

4-(2,6-dichloro-4-pyridyl)-3-methyl-morpholine

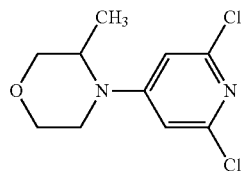

2,6-dichloro-4-iodo-pyridine (1.5 g, 5.48 mmol), 3-methylmorpholine (0.61 ml, 6.02 mmol), PPh$_3$ (143.65 mg, 0.55 mmol), Pd(OAc)$_2$ (61.48 mg, 0.27 mmol) and freshly ground K$_3$PO$_4$ (3.49 g, 16.43 mmol) were taken up in DMF (30 ml) and the resulting mixture was stirred at 100° C. for 1 h. When cooled to rt the mixture was poured into water (50 ml) and extracted with EtOAc (3×15 ml). The combined organics were washed with brine, dried over Na$_2$SO$_4$, filtered, concentrated and purified on a silica gel column eluted with 0-60% EtOAc in Heptane to give the product as a solid (800 mg, 59%). MS ES+ m/z 247 [M+H]$^+$.

Intermediate Example 5

4-(2-tert-butoxy-6-chloro-4-pyridyl)-3-methyl-morpholine

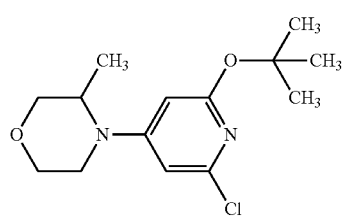 [SMILES: CC1COCCN1c1cc(Cl)nc(OC(C)(C)C)c1]

4-(2,6-dichloro-4-pyridyl)-3-methyl-morpholine (2.2 g, 8.9 mmol), KOtBu (2.5 g, 22.26 mmol) and 4 Å molecular sieves were taken up in anh. Toluene (40 ml) and stirred at 90° C. for 2 h. When cooled to rt the mixture was diluted with EtOAc (30 ml), brine (40 ml) and water (20 ml). The organic layer was separated and the aqueous layer extracted with EtOAc (2×25 ml). The combined organics were washed with brine, dried over Na$_2$SO$_4$, filtered, concentrated and purified on a silica gel column eluted with 0-40% EtOAc in Heptane to give the product as an oil (2.2 g, 87%). MS ES+ m/z 285 [M+H]$^+$.

Example 5

4-(3-methylmorpholin-4-yl)-6-(4-methyl-3-pyridyl)-1H-pyridin-2-one

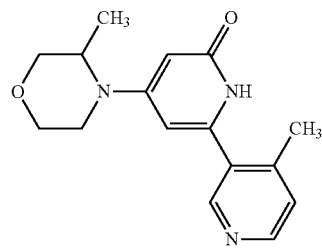 [SMILES: Cc1ccncc1-c1cc(N2CCOCC2C)cc(=O)[nH]1]

4-(2-tert-butoxy-6-chloro-4-pyridyl)-3-methyl-morpholine (0.14 g, 0.51 mmol), (4-methyl-3-pyridyl)boronic acid (0.08 g, 0.61 mmol), PdCl$_2$(amphos) (3.58 mg, 5.06 µmol) and K$_2$CO$_3$ (209.65 mg, 1.52 mmol) were dissolved in 2-MeTHF (3 ml) and water (1 ml). The resulting mixture was heated in a microwave reactor at 140° C. for 40 min. More PdCl$_2$(amphos) (3.58 mg, 5.06 µmol) and (4-methyl-3-pyridyl)boronic acid (0.03 g) were added and the mixture heated again at 140° C. for 60 min. When cooled to rt brine (5 ml) and EtOAc (5 ml) were added. The organic layer was separated and the aqueous layer extracted with EtOAc (2×10 ml). The combined organics were washed with brine, dried over MgSO$_4$, filtered and concentrated. The resulting residue was taken up in DCM (5 ml), TFA (345.93 mg, 3.03 mmol) was added and the mixture was stirred at rt overnight. The mixture was concentrated and purified by preparative HPLC to give the product as a solid (40 mg, 28%). $^1$H NMR (400 MHz, DMSO-d$_6$) 8.48 (d, 1H), 8.43 (s, 1H), 7.33 (d, 1H), 6.04 (s, 1H), 5.40 (s, 1H), 3.97 (br d, 1H), 3.88 (dd, 1H), 3.69-3.57 (m, 2H), 3.51-3.35 (m, 2H), 3.04 (td, 1H), 2.30 (s, 3H), 1.12 (d, 3H). MS ES+ m/z 286 [M+H]$^+$.

Example 6

4-(3-methylmorpholin-4-yl)-6-pyrimidin-5-yl-1H-pyridin-2-one

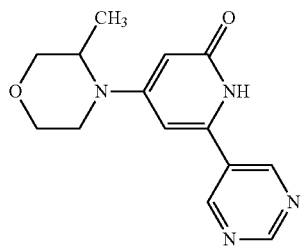 [SMILES: CC1COCCN1c1cc(-c2cncnc2)[nH]c(=O)c1]

4-(2-tert-butoxy-6-chloro-4-pyridyl)-3-methyl-morpholine (0.14 g, 0.51 mmol), pyrimidin-5-ylboronic acid (0.08 g, 0.61 mmol), PdCl$_2$(amphos) (3.58 mg, 5.06 µmol) and K$_2$CO$_3$ (209.65 mg, 1.52 mmol) were dissolved in 2-MeTHF (3 ml) and water (1 ml). The resulting mixture was heated in a microwave reactor at 140° C. for 40 min. More PdCl$_2$(amphos) (3.58 mg, 5.06 µmol) and pyrimidin-5-ylboronic acid (0.03 g) were added and the mixture was heated at 140° C. for 60 min. When cooled to rt brine (5 ml), water (4 ml) and EtOAc (5 ml) were added. The organic layer was separated and the aqueous layer was extracted with EtOAc (2×10 ml). The combined organics were washed with brine, dried over MgSO$_4$, filtered and concentrated. The resulting residue was taken up in DCM (5 ml) and TFA (345.93 mg, 3.03 mmol) was added. The mixture was stirred at rt overnight. The mixture was concentrated and purified by preparative HPLC to give the product as a solid (60 mg, 42%). $^1$H NMR (400 MHz, DMSO-d$_6$) 11.05 (br s, 1H), 9.22 (s, 1H), 9.17 (s, 2H), 6.63 (s, 1H), 5.56 (s, 1H), 4.08 (br d, 1H), 3.91 (br d, 1H), 3.73-3.67 (m, 1H), 3.66-3.60 (m, 1H), 3.53-3.44 (m, 2H), 3.12-3.02 (m, 1H), 1.12 (d, 3H). MS ES+ m/z 273 [M+H]$^+$.

Example 7

4-(3-methylmorpholin-4-yl)-6-(2-phenylphenyl)-1H-pyridin-2-one

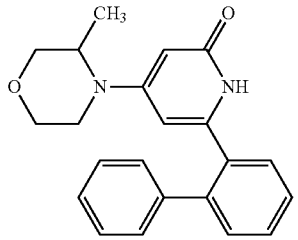 [SMILES: CC1COCCN1c1cc(-c2ccccc2-c2ccccc2)[nH]c(=O)c1]

4-(2-tert-butoxy-6-chloro-4-pyridyl)-3-methyl-morpholine (0.09 g, 0.32 mmol), (2-phenylphenyl)boronic acid (0.08 g, 0.38 mmol), K$_2$CO$_3$ (131.03 mg, 0.95 mmol) and PdCl$_2$(amphos) (2.24 mg, 3.16 μmol) were dissolved in 2-MeTHF (3 ml) and Water (1 ml). The resulting mixture was heated in a microwave reactor at 140° C. for 60 min. When cooled to rt the organic layer was filtered and concentrated. The resulting residue was taken up in DCM (5 ml), TFA (0.28 g, 2.48 mmol) was added and the mixture was stirred at rt overnight. The mixture was concentrated and purified by preparative HPLC to give the product as a solid (12 mg, 14%). $^1$H NMR (500 MHz, DMSO-d$_6$) δ 10.80 (br s, 1H), 7.55-7.50 (m, 1H), 7.47 (d, 2H), 7.42 (d, 1H), 7.38-7.32 (m, 2H), 7.32-7.24 (m, 3H), 5.65 (d, 1H), 5.24 (d, 1H), 3.82 (br dd, 1H), 3.66 (br d, 1H), 3.57 (d, 1H), 3.50 (dd, 1H), 3.38 (td, 1H), 3.14 (br d, 1H), 2.86 (td, 1H), 0.82 (d, 3H). MS ES+ m/z 347 [M+H]$^+$.

Intermediate Example 6

(3R)-4-(2,6-dichloro-4-pyridyl)-3-methyl-morpholine

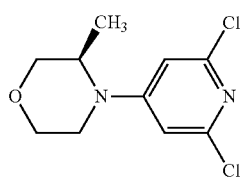

The title compound was prepared as described in intermediate example 4, replacing 3-methylmorpholine with (R)-3-methylmorpholine, to give the product as a solid (900 mg, 66%). MS ES+ m/z 247 [M+H]$^+$.

Intermediate Example 7

(3R)-4-(2-tert-butoxy-6-chloro-4-pyridyl)-3-methyl-morpholine

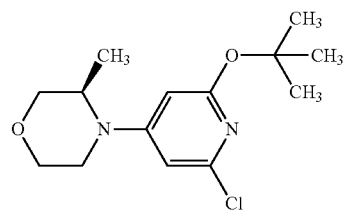 [SMILES: C[C@@H]1COCCN1c1cc(Cl)nc(OC(C)(C)C)c1]

The title compound was prepared as described in intermediate example 5, starting from (3R)-4-(2,6-dichloro-4-pyridyl)-3-methyl-morpholine (700 mg), to give the product as an oil (510 mg, 63%). $^1$H NMR (400 MHz, CDCl$_3$) δ 6.29 (s, 1H), 5.92-5.81 (m, 1H), 4.04-3.92 (m, 1H), 3.85-3.69 (m, 3H), 3.65-3.52 (m, 1H), 3.29-3.10 (m, 2H), 1.59-1.53 (m, 9H), 1.21 (d, 3H). MS ES+ m/z 285 [M+H]$^+$.

Intermediate Example 8

(3R)-4-[2-tert-butoxy-6-(2-chloro-5-fluoro-phenyl)-4-pyridyl]-3-methyl-morpholine

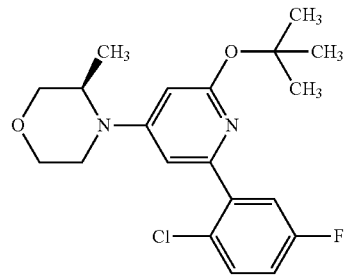 [SMILES: C[C@@H]1COCCN1c1cc(OC(C)(C)C)nc(-c2cc(F)ccc2Cl)c1]

To a solution of (3R)-4-(2-tert-butoxy-6-chloro-4-pyridyl)-3-methyl-morpholine (1.0 g, 3.52 mmol) in 1,4-Dioxane (10 ml) at rt, (2-chloro-5-fluoro-phenyl)boronic acid (735 mg, 4.2 mmol) and aq. 0.5M K$_3$PO$_4$ solution (5 ml) were added and the resulting mixture was degassed with nitrogen for 15 min. Chloro(2-dicyclohexylphosphino-2',4',6'-triisopropyl-1,1'-biphenyl)[2-(2'-amino-1,1'-biphenyl)]palladium(II) (110 mg, 0.35 mmol) was added and the reaction mixture was heated in a microwave reactor at 100° C. for 1 h. When cooled to rt the mixture was filtered through Celite® and the filtrate was diluted with water and extracted with EtOAc. The organic layer was washed with brine, dried over Na$_2$SO$_4$, filtered, concentrated and purified by preparative HPLC to give the product (150 mg, 11%). MS ES+ m/z 379 [M+H]$^+$.

Example 8

6-(2-chloro-5-fluoro-phenyl)-4-[(3R)-3-methylmorpholin-4-yl]-1H-pyridin-2-one

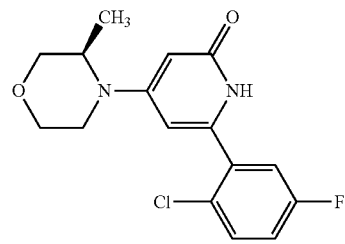 [SMILES: C[C@@H]1COCCN1c1cc(-c2cc(F)ccc2Cl)[nH]c(=O)c1]

TFA (0.3 ml, 3.9 mmol) was added to a solution of (3R)-4-[2-tert-butoxy-6-(2-chloro-5-fluoro-phenyl)-4-pyridyl]-3-methyl-morpholine (150 mg, 0.39 mmol) in DCM (10 ml) at 0° C. and the mixture was stirred at rt overnight. pH was adjusted above 7 using sat. aq. NaHCO$_3$ and the mixture was extracted with DCM. The organic layer was washed with brine, dried over Na$_2$SO$_4$, filtered, concentrated and purified on silica gel eluting with 0-5% MeOH in DCM to give the product as a solid (60 mg, 47%). $^1$H NMR (400 MHz, CDCl$_3$) 7.45 (dd, 1H), 7.20-7.17 (m, 1H), 7.13-7.08 (m, 1H), 6.00 (d, 1H), 5.64 (d, 1H), 4.00 (dd, 1H), 3.85-3.72 (m, 3H), 3.61 (dt, 1H), 3.33-3.20 (m, 2H), 1.27 (d, 3H). MS ES+ m/z 323 [M+H]$^+$.

Example 9

4-[(3R)-3-methylmorpholin-4-yl]-6-(o-tolyl)-1H-pyridin-2-one

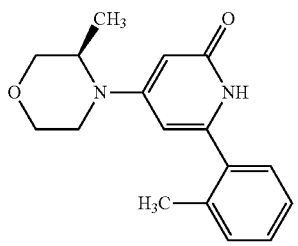 [SMILES: Cc1ccccc1-c1cc(N2CCOC[C@H]2C)cc(=O)[nH]1]

A mixture of (3R)-4-(2-tert-butoxy-6-chloro-4-pyridyl)-3-methyl-morpholine (0.5 g, 1.76 mmol), o-tolylboronic acid (713 mg, 5.3 mmol), K$_2$CO$_3$ (729 mg, 5.3 mmol) and PdCl$_2$(amphos) (31 mg, 0.17 mmol) in 2-MeTHF:H$_2$O (3:1, 4 ml) was degassed with nitrogen for 15 min. The reaction mixture was heated in a microwave reactor at 160° C. for 4 h. When cooled to rt the mixture was filtered through Celite® and the filtrate was diluted with water and extracted with EtOAc. The organic layer was washed with brine, dried over Na$_2$SO$_4$, filtered, concentrated and purified by preparative HPLC (using 0.1% HCOOH in MeCN) to give crude product (70 mg). The crude product was further purified by preparative TLC to give the product as a solid (35 mg, 7%). $^1$H NMR (400 MHz, CDCl$_3$) 7.35 (br d, 1H), 7.28 (br s, 3H), 5.86 (s, 1H), 5.63 (br s, 1H), 4.00 (br dd, 1H), 3.81 (br s, 1H), 3.77-3.75 (m, 1H), 3.76 (s, 1H), 3.65-3.59 (m, 1H), 3.28 (br d, 2H), 2.36 (s, 3H), 1.27 (br d, 3H). MS ES+ m/z 285 [M+H]$^+$.

Example 10

4-[(3R)-3-methylmorpholin-4-yl]-6-[2-(trifluoromethyl)-3-pyridyl]-1H-pyridin-2-one

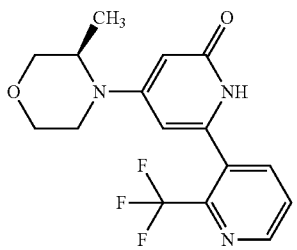 [SMILES: C[C@@H]1COCCN1c1cc(-c2cccnc2C(F)(F)F)[nH]c(=O)c1]

A mixture of (3R)-4-(2-tert-butoxy-6-chloro-4-pyridyl)-3-methyl-morpholine (0.25 g, 0.88 mmol), [2-(trifluoromethyl)-3-pyridyl]boronic acid (501 mg, 2.6 mmol), K$_2$CO$_3$ (364 mg, 2.6 mmol) and PdCl$_2$(amphos) (16 mg, 0.08 mmol) in 2-MeTHF:H$_2$O (3:1, 3 ml) was degassed with nitrogen for 15 min. The reaction mixture was heated in a microwave reactor at 160° C. for 4 h. When cooled to rt the mixture was filtered through Celite® and the filtrate was diluted with water and extracted with EtOAc. The organic layer was washed with brine, dried over Na$_2$SO$_4$, filtered, concentrated and purified by preparative HPLC. TFA (0.06 ml, 0.76 mmol) was added to a solution of the crude product in DCM (1 ml) and the resulting mixture was stirred at rt overnight. pH was adjusted above 7 using sat. aq. NaHCO$_3$ and the mixture was extracted with DCM. The organic layer was washed with brine, dried over Na$_2$SO$_4$, filtered, concentrated and purified on silica gel eluting with 0-5% MeOH in DCM to give the product as a solid (5 mg, 2%). $^1$H NMR (400 MHz, CDCl$_3$) δ 10.83 (br s, 1H), 8.82 (br d, 1H), 7.92 (br d, 1H), 7.63 (dd, 1H), 5.94 (d, 1H), 5.62 (s, 1H), 3.99 (br d, 1H), 3.81-3.74 (m, 3H), 3.60 (dt, 1H), 3.30-3.18 (m, 2H), 1.25 (br d, 3H). MS ES+ m/z 340 [M+H]$^+$.

Example 11

6-(2-chlorophenyl)-4-[(3R)-3-methylmorpholin-4-yl]-1H-pyridin-2-one

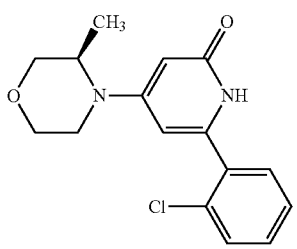 [SMILES: C[C@@H]1COCCN1c1cc(-c2ccccc2Cl)[nH]c(=O)c1]

A mixture of (2-chlorophenyl)boronic acid (769 mg, 4.9 mmol), Chloro(2-dicyclohexylphosphino-2',4',6'-triisopropyl-1,1'-biphenyl)[2-(2'-amino-1,1'-biphenyl)]palladium(II) (110 mg, 0.35 mmol), aq. 0.5M K$_3$PO$_4$ solution (5 ml) in THF (10 ml) degassed with argon for 15 min. (3R)-4-(2-tert-butoxy-6-chloro-4-pyridyl)-3-methyl-morpholine (1.0 g, 3.52 mmol) was added and the resulting mixture was heated in a microwave reactor at 100° C. for 1 h. When cooled to rt the mixture was filtered through Celite® and the filtrate was diluted with water and extracted with EtOAc. The organic layer was washed with brine, dried over Na₂SO₄, filtered, concentrated and purified by preparative HPLC (using 0.1% HCOOH in MeCN) to give crude product (85 mg). The crude product was further purified by preparative TLC to give the product as a solid (45 mg, 4%). ¹H NMR (400 MHz, CDCl₃) δ 7.50 (br d, 1H), 7.43-7.34 (m, 3H), 6.01 (s, 1H), 5.66 (br s, 1H), 4.02-3.98 (m, 1H), 3.86-3.75 (m, 3H), 3.61 (dt, 1H), 3.35-3.23 (m, 2H), 1.28 (d, 3H). MS ES+ m/z 305 [M+H]⁺.

Example 12

4-[(3R)-3-methylmorpholin-4-yl]-6-[2-(trifluoromethyl)phenyl]-1H-pyridin-2-one

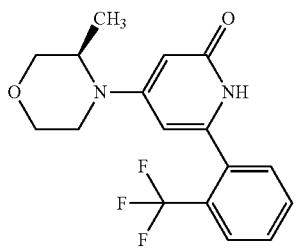 [SMILES: C[C@@H]1COCCN1c1cc(-c2ccccc2C(F)(F)F)[nH]c(=O)c1]

The title compound was prepared as described in Example 9, replacing o-tolylboronic acid with [2-(trifluoromethyl)phenyl]boronic acid, to give the product as a solid (50 mg, 8%). ¹H NMR (400 MHz, CDCl₃) 7.79 (d, 1H), 7.68-7.57 (m, 2H), 7.50 (br d, 1H), 5.92 (d, 1H), 5.63 (d, 1H), 3.99 (br dd, 1H), 3.81-3.74 (m, 3H), 3.60 (td, 1H), 3.30-3.18 (m, 2H), 1.25 (d, 3H). MS ES+ m/z 339 [M+H]⁺.

Example 13

6-(3-furyl)-4-[(3R)-3-methylmorpholin-4-yl]-1H-pyridin-2-one

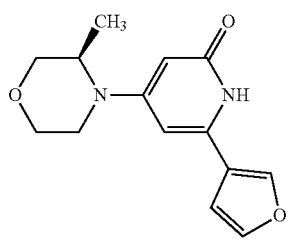 [SMILES: C[C@@H]1COCCN1c1cc(-c2ccoc2)[nH]c(=O)c1]

The title compound was prepared as described in Example 9, replacing o-tolylboronic acid with 3-furylboronic acid, to give the product as a solid (40 mg, 14%). ¹H NMR (400 MHz, CDCl₃) δ 8.37 (s, 1H), 7.49 (s, 1H), 6.76 (s, 1H), 6.08 (d, 1H), 5.65 (d, 1H), 4.02 (dd, 1H), 3.89 (br d, 1H), 3.82-3.74 (m, 2H), 3.63 (td, 1H), 3.37-3.22 (m, 2H), 1.27 (d, 3H). MS ES+ m/z 261 [M+H]⁺.

Example 14

4-[(3R)-3-methylmorpholin-4-yl]-6-(4-methyl-3-thienyl)-1H-pyridin-2-one

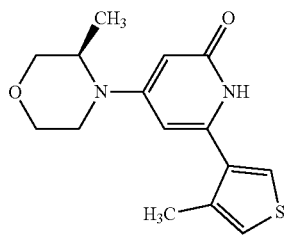 [SMILES: Cc1cscc1-c1cc(N2CCOC[C@H]2C)cc(=O)[nH]1]

The title compound was prepared as described in Example 9, replacing o-tolylboronic acid with (4-methyl-3-thienyl)boronic acid, to give the product as a solid (50 mg, 10%). ¹H NMR (400 MHz, CDCl₃) 8.70 (br s, 1H), 7.45 (d, 1H), 7.07 (br s, 1H), 5.93 (s, 1H), 5.63 (br s, 1H), 4.00 (br dd, 1H), 3.85-3.75 (m, 3H), 3.61 (td, 1H), 3.34-3.20 (m, 2H), 2.33 (s, 3H), 1.27 (d, 3H). MS ES+ m/z 291 [M+H]⁺.

Intermediate Example 9

N-[2-[6-tert-butoxy-4-[(3R)-3-methylmorpholin-4-yl]-2-pyridyl]phenyl]methanesulfonamide

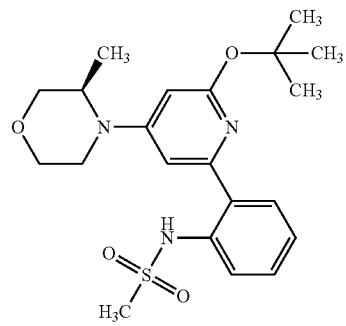 [SMILES: C[C@@H]1COCCN1c1cc(OC(C)(C)C)nc(-c2ccccc2NS(C)(=O)=O)c1]

A solution of (3R)-4-(2-tert-butoxy-6-chloro-4-pyridyl)-3-methyl-morpholine (300 mg, 1.05 mmol), [2-(methanesulfonamido)phenyl]boronic acid (300 mg, 1.26 mmol) and Na₂CO₃ (350 mg, 3.16 mmol) in 1,4-Dioxane and water (1:1, 10 ml) was degassed with nitrogen for 10 min. PdCl₂ (dppf), DCM adduct (80 mg, 0.11 mmol) was added and the mixture was heated in a microwave reactor at 130° C. for 1.5 h. Water (10 ml) was added and the mixture extracted with EtOAc (3×15 ml). The combined organics were washed with brine, dried over Na₂SO₄, filtered, concentrated and purified on a silica gel column eluted with 20-30% EtOAc in Heptane to give the product (200 mg, 43%). LCMS ES+ m/z 420 [M+H]⁺.

Example 15

N-[2-[4-[(3R)-3-methylmorpholin-4-yl]-6-oxo-1H-pyridin-2-yl]phenyl]methanesulfonamide

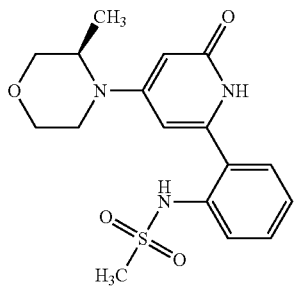 [SMILES: C[C@@H]1COCCN1c1cc(-c2ccccc2NS(C)(=O)=O)[nH]c(=O)c1]

TFA (1 ml, 13.07 mmol) was added to solution of N-[2-[6-tert-butoxy-4-[(3R)-3-methylmorpholin-4-yl]-2-pyridyl]phenyl]methanesulfonamide (300 mg, 0.71 mmol) in DCM (30 ml) and the resulting mixture was stirred at rt overnight. The mixture was cooled to 0° C. and pH adjusted to 8 using sat. aq. NaHCO$_3$. The organic layer was separated and the aqueous layer extracted with DCM (2×15 ml). The combined organics were washed with brine, dried over Na$_2$SO$_4$, filtered, concentrated and purified on a silica gel column eluted with 10% MeOH in DCM to give the product as a solid (140 mg, 53%). $^1$H NMR (400 MHz, DMSO-d$_6$): δ 10.95-10.40 (bs, 1H), 7.87 (d, 1H), 7.69-7.62 (m, 2H), 7.50-7.37 (bs, 2H), 6.00-5.98 (bs, 1H), 5.42-5.39 (bs, 1H), 3.90-3.84 (dd, 2H), 3.65-3.56 (m, 2H), 3.50-3.45 (m, 1H), 3.17-3.05 (m, 1H), 2.5 (d, 3H), 1.19-1.10 (m 3H). LCMS ES+ m/z 364 [M+H]$^+$.

Intermediate Example 10

(3R)-4-[2-tert-butoxy-6-(6-methyl-5-quinolyl)-4-pyridyl]-3-methyl-morpholine

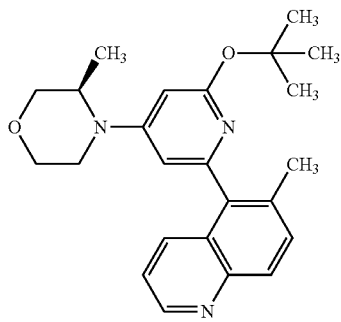 [SMILES: Cc1ccc2ncccc2c1-c1cc(N2CCOC[C@H]2C)cc(OC(C)(C)C)n1]

The title compound was prepared as described in Example 15, replacing [2-(methanesulfonamido)phenyl]boronic acid with (6-methyl-5-quinolyl)boronic acid, to give the product (180 mg, 43%). LCMS ES+ m/z 392 [M+H]$^+$.

Example 16

4-[(3R)-3-methylmorpholin-4-yl]-6-(6-methyl-5-quinolyl)-1H-pyridin-2-one

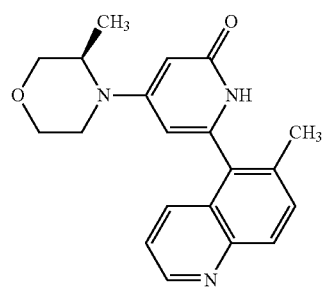 [SMILES: Cc1ccc2ncccc2c1-c1cc(N2CCOC[C@H]2C)cc(=O)[nH]1]

The title compound was prepared as described in Example 16, starting from (3R)-4-[2-tert-butoxy-6-(6-methyl-5-quinolyl)-4-pyridyl]-3-methyl-morpholine (180 mg, 0.46 mmol), to give the product as a solid (85 mg, 59%). $^1$H NMR (400 MHz, DMSO-d$_6$): δ 10.94 (s, 1H), 8.87 (d, 1H), 8.01 (d, 1H), 7.91 (d, 1H), 7.71 (m, 1H), 6.03 (bs, 1H) 5.45 (bs, 1H), 3.94 (m, 1H), 3.88-3.86 (d, 2H), 3.64-3.45 (m, 2H), 3.40 (m, 1H) 3.01-3.17 (t, 1H), 2.37 (s. 3H), 1.20 (d, 3H). LCMS ES+ m/z 336 [M+H]$^+$.

Intermediate Example 11

5-[4-(4,4,5,5-tetramethyl-1,3,2-dioxaborolan-2-yl)phenyl]-1H-pyrazole

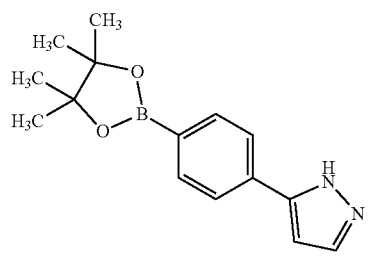 [SMILES: CC1(C)OB(c2ccc(-c3ccn[nH]3)cc2)OC1(C)C]

A solution of 5-(4-bromophenyl)-1H-pyrazole (250 mg, 0.88 mmol), Bis(pinacolato)diboron (268 mg, 1.05 mmol) and KOAc (260 mg, 2.63 mmol) in 1,4-Dioxane (10 ml) was degassed with nitrogen for 10 min. PdCl$_2$(dppf), DCM adduct (65 mg, 0.09 mmol) was added and the mixture was heated in a microwave reactor at 120° C. for 2 h. Water (10 ml) was added and the mixture extracted with EtOAc (3×10 ml). The combined organics were washed with brine, dried over Na$_2$SO$_4$, filtered, concentrated and purified on a silica gel column eluted with 25-30% EtOAc in Heptane to give the product (150 mg, 50%). LCMS ES+ m/z 271 [M+H]$^+$.

Intermediate Example 12

(3R)-4-[2-tert-butoxy-6-[4-(1H-pyrazol-5-yl)phenyl]-4-pyridyl]-3-methyl-morpholine

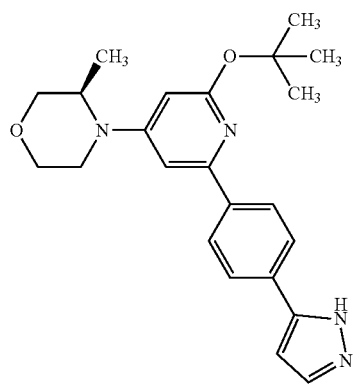 [SMILES: C[C@@H]1COCCN1c1cc(OC(C)(C)C)nc(-c2ccc(-c3ccn[nH]3)cc2)c1]

The title compound was prepared as described in Example 15, replacing [2-(methanesulfonamido)phenyl]boronic acid with 5-[4-(4,4,5,5-tetramethyl-1,3,2-dioxaborolan-2-yl)phenyl]-1H-pyrazole, to give the product (120 mg, 17%). LCMS ES+ m/z 393 [M+H]+.

Example 17

4-[(3R)-3-methylmorpholin-4-yl]-6-[4-(1H-pyrazol-5-yl)phenyl]-1H-pyridin-2-one

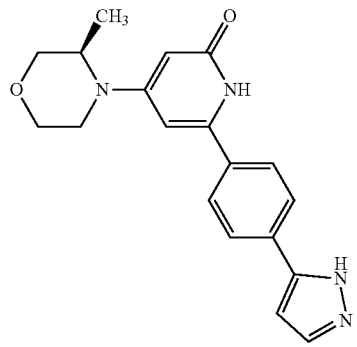 [SMILES: C[C@@H]1COCCN1c1cc(-c2ccc(-c3ccn[nH]3)cc2)[nH]c(=O)c1]

The title compound was prepared as described in Example 16, starting from (3R)-4-[2-tert-butoxy-6-[4-(1H-pyrazol-5-yl)phenyl]-4-pyridyl]-3-methyl-morpholine (200 mg, 0.51 mmol), to give the product as a solid (125 mg, 70%). $^1$H NMR (400 MHz, DMSO-$d_6$): δ 12.95 (bs, 1H), 10.91 (bs, 1H), 7.88-7.77 (dd, 5H), 6.80 (d, 1H), 6.37 (s, 1H), 5.42 (s, 1H), 4.06 (d, 1H), 3.90 (d, 1H), 3.71-3.62 (m, 2H), 3.52-3.45 (m, 2H), 3.10-3.05 (m, 1H), 1.13-1.12 (m, 3H). LCMS ES+ m/z 337 [M+H]+.

Example 18

Vps34 Biochemical Assay

Dilution series of compounds of the invention were prepared in DMSO at 100 times the final assay concentration ($n_1=n_0/3$ in 10 points). The compounds were further diluted to 4 times the assay concentration in assay buffer (Life technologies buffer Q, PV5125, diluted 5 times supplemented with 2 mM DTT and 2 mM $MnCl_2$). 2.5 µl of the diluted compounds were added to a 384 well assay plate followed by 2.5 µl of 16.5 nM Vps34 enzyme (Life technologies, PV5126). Enzyme and compounds were preincubated at rt for 15 min. Then 5 µl of substrate mix containing 20 µM ATP (Life technologies, PV3227) and 200 µM PI:PS substrate (Life technologies, PV5122) in assay buffer was added to the wells containing compound and enzyme and mixing was performed by pipetting several times. The reaction was incubated at room temperature for 1 h. Then 5 µl stop-detection mix, prepared as described in the adapta kinase assay kit instructions (Life technologies, PV5099) containing Adapta Eu-anti-ADP antibody (2.3 nM), Alexa Fluor 647 ADP tracer (9 nM) and EDTA (30 mM) in TR-FRET buffer, was added to quench the reaction. Mixing was performed by pipetting several times. The assay plate was then incubated at room temperature for 30 min and read with Artemis micro plate reader. Percent inhibition of the compounds as compared to DMSO treated control samples was calculated. By the use of Dotmatics software compound concentration versus percent inhibition was fitted to generate $IC_{50}$ values.

The example compounds effectively inhibited Vps34 and the results of the assay are shown in Table 1 (Median $IC_{50}$ µM Adapta).

TABLE 1

| Median $IC_{50}$ values for the Vps34 assay | |
|---|---|
| Example Compound | Median $IC_{50}$ µM Adapta |
| 1 | 0.03 |
| 2 | 0.05 |
| 3 | 0.01 |
| 4 | 0.02 |
| 5 | 0.1 |
| 6 | 1 |
| 7 | 0.06 |
| 8 | 0.01 |
| 9 | 0.03 |
| 10 | 0.02 |
| 11 | 0.007 |
| 12 | 0.007 |
| 13 | 0.2 |
| 14 | 0.03 |
| 15 | 0.2 |
| 16 | 0.2 |
| 17 | 0.2 |

Example 19

High Content Screening Autophagy Assay

Human osteosarcoma cells (HOS) stably expressing a Green Fluorescent Protein (GFP) tagged LC3 (GFP-LC3) were used to determine the inhibitory effect on autophagy of proprietary compounds. For that purpose, autophagy was activated by using the mTOR inhibitor KU-0063794 at 500 nM in the presence of Bafilomycin A1 (Sigma-Aldrich) at 5 nM. Shortly, cells were plated overnight in clear bottom 96-well plates in DMEM-High Modified media (Hi-Clone Cat #SH30285.01). At the start of the experiment, the media was removed and replaced with fresh media containing the mTOR inhibitor, Bafilomycin A1 and the vehicle or a test compound as indicated. After 6 hours the media was removed, cells were washed twice with ice-cold phosphate buffered saline (PBS) and fixed with 4% paraformaldehyde for 20 minutes at room temperature. Then the cells were washed twice with ice-cold PBS before adding Hoechst 33342 at 1 μg/ml in PBS for nuclear staining. After incubation overnight at 4° C., cells were washed once with PBS to remove the excess of dye and 100 μl of PBS was added to each well. Images were acquired at 20× magnification, 6 images per well, using the ImageXpress automated microscope (Molecular Devices Inc.) and analyzed with MetaXpress software to identify LC3-GFP foci. Foci area per cell values were used to generate dose response curves and IC50 calculated using non-linear fitting analysis in GraphPad Prism software.

The tested example compounds effectively inhibited autophagy in HOS cells. The results of the assay are shown in Table 2 (Median $IC_{50}$ μM Cellular assay).

TABLE 2

Median $IC_{50}$ values for the Vps34 assay and autophagy in HOS cells assay.

| Example Compound | Median $IC_{50}$ μM Cellular assay |
|---|---|
| 1 | 2 |
| 2 | 3 |
| 3 | 0.7 |
| 4 | 1 |
| 5 | 14 |
| 6 | 14 |
| 8 | 1 |
| 10 | 0.09 |
| 11 | 0.6 |
| 12 | 0.6 |

The invention claimed is:

1. A compound of formula (I)

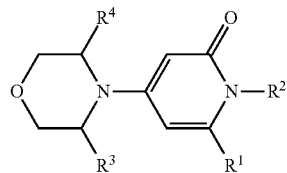

I wherein
$R^1$ is aryl or heteroaryl, said aryl and said heteroaryl being mono- or bicyclic and optionally substituted with one or more of $R^5$, $R^6$, $R^7$ and $R^8$;
$R^2$, $R^3$ and $R^4$ are independently selected from hydrogen, $C_1$-$C_3$haloalkyl and $C_1$-$C_3$alkyl;
$R^5$, $R^6$, $R^7$ and $R^8$ are independently selected from halogen, $C_1$-$C_6$alkyl, $C_1$-$C_6$alkoxy, $C_1$-$C_6$haloalkyl, amino, —$NHSO_2R^9$, hydroxy, phenyl and a monocyclic heteroaryl;
$R^9$ is $C_1$-$C_3$haloalkyl or $C_1$-$C_3$alkyl;
and pharmaceutically acceptable salts, tautomers and stereoisomers thereof.

2. The compound according to claim 1, wherein $R^4$ is $C_1$-$C_3$alkyl.

3. The compound according to claim 1, wherein $R^2$ is selected from hydrogen and methyl.

4. The compound according to claim 1, wherein $R^3$ is hydrogen.

5. The compound according to claim 1, wherein $R^4$ is methyl.

6. The compound according to claim 1, wherein $R^2$ is hydrogen.

7. The compound according to claim 1, wherein $R^1$ is selected from phenyl, furyl, thienyl, pyridyl, pyrimidinyl, naphtyl, quinolinyl, indazolyl, indolyl, 4-azaindolyl, benzoxazolyl, benzimidazolyl, benzothiophenyl, each optionally substituted with one or more of $R^5$, $R^6$, $R^7$ and $R^8$; and
$R^5$, $R^6$, $R^7$ and $R^8$ are independently selected from halogen, $C_1$-$C_3$alkyl, $C_1$-$C_3$haloalkyl, phenyl, amino, —$NHSO_2CH_3$, hydroxy, imidazolyl and pyrazolyl.

8. The compound according to claim 1, wherein $R^1$ is selected from phenyl, furyl, thienyl, pyridyl, pyrimidinyl and quinolinyl, each optionally substituted with $R^5$ and/or $R^6$; and $R^5$ and $R^6$ are independently selected from chlorine, fluorine, trifluoromethyl, methyl, phenyl, —$NHSO_2CH_3$ and pyrazolyl.

9. The compound according to claim 1, wherein $R^1$ is selected from

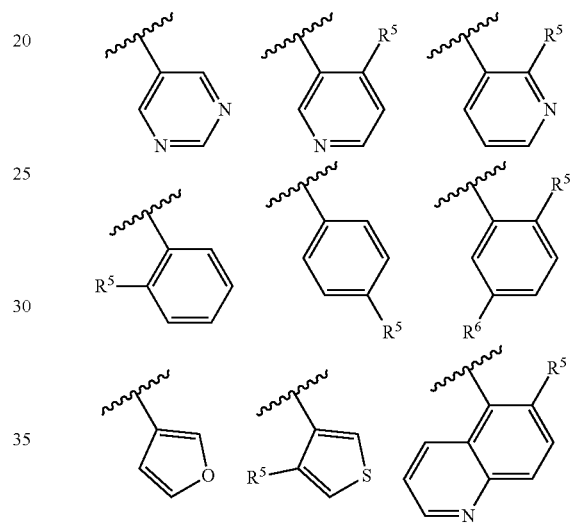

wherein $R^5$ and $R^6$ are independently selected from halogen, $C_1$-$C_3$alkyl, $C_1$-$C_3$haloalkyl, phenyl, pyrazolyl, and —$NHSO_2CH_3$.

10. The compound according to claim 1, wherein $R^1$ is a monocyclic aryl or heteroaryl.

11. The compound according to claim 1, wherein $R^1$ is selected from phenyl and pyridyl, each optionally substituted with $R^5$ and/or $R^6$; and $R^5$ and $R^6$ are independently selected from chlorine, fluorine and trifluoromethyl.

12. The compound according to claim 1, wherein $R^1$ is selected from

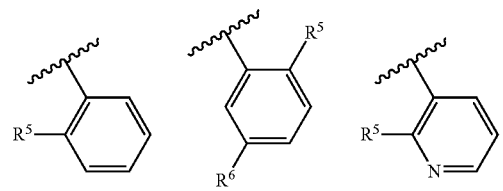

$R^4$ is $C_1$-$C_3$alkyl;
and $R^5$ and $R^6$ are independently selected from chlorine, fluorine and trifluoromethyl.

13. The compound according to claim 1, wherein $R^1$ is selected from

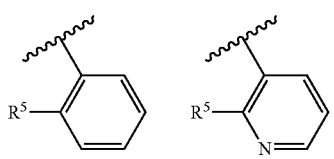

$R^2$ is hydrogen; and
$R^5$ is selected from chlorine and trifluoromethyl.

14. The compound according to claim 1, wherein $R^1$ is selected from

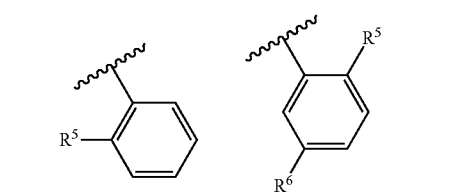

$R^2$ is hydrogen;
$R^4$ is $C_1$-$C_3$alkyl; and
$R^5$ and $R^6$ are independently selected from chlorine, fluorine and trifluoromethyl.

15. The compound according to claim 1, wherein $R^1$ is selected from

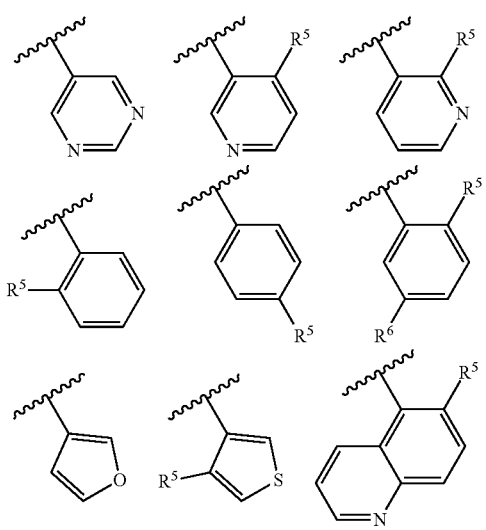

$R^2$ is hydrogen or methyl;
$R^3$ is hydrogen;
$R^4$ is methyl;
$R^5$ and $R^6$ are selected from chlorine, fluorine, trifluoromethyl, methyl, phenyl pyrazolyl and —NHSO$_2$CH$_3$; and
pharmaceutically acceptable salts and stereoisomers thereof.

16. The compound according to claim 1, said compound being selected from:

6-(2-chlorophenyl)-4-morpholino-1H-pyridin-2-one;
6-(2-chlorophenyl)-1-methyl-4-morpholino-pyridin-2-one;
6-(2-chlorophenyl)-4-(3-methylmorpholin-4-yl)-1H-pyridin-2-one;
6-(2-chlorophenyl)-1-methyl-4-(3-methylmorpholin-4-yl)pyridin-2-one;
4-(3-methylmorpholin-4-yl)-6-(4-methyl-3-pyridyl)-1H-pyridin-2-one;
4-(3-methylmorpholin-4-yl)-6-pyrimidin-5-yl-1H-pyridin-2-one;
4-(3-methylmorpholin-4-yl)-6-(2-phenylphenyl)-1H-pyridin-2-one;
6-(2-chloro-5-fluoro-phenyl)-4-[(3R)-3-methylmorpholin-4-yl]-1H-pyridin-2-one;
4-[(3R)-3-methylmorpholin-4-yl]-6-(o-tolyl)-1H-pyridin-2-one;
4-[(3R)-3-methylmorpholin-4-yl]-6-[2-(trifluoromethyl)-3-pyridyl]-1H-pyridin-2-one;
6-(2-chlorophenyl)-4-[(3R)-3-methylmorpholin-4-yl]-1H-pyridin-2-one;
4-[(3R)-3-methylmorpholin-4-yl]-6-[2-(trifluoromethyl)phenyl]-1H-pyridin-2-one;
6-(3-furyl)-4-[(3R)-3-methylmorpholin-4-yl]-1H-pyridin-2-one;
4-[(3R)-3-methylmorpholin-4-yl]-6-(4-methyl-3-thienyl)-1H-pyridin-2-one;
N-[2-[4-[(3R)-3-methylmorpholin-4-yl]-6-oxo-1H-pyridin-2-yl]phenyl]methanesulfonamide;
4-[(3R)-3-methylmorpholin-4-yl]-6-(6-methyl-5-quinolyl)-1H-pyridin-2-one;
4-[(3R)-3-methylmorpholin-4-yl]-6-[4-(1H-pyrazol-5-yl)phenyl]-1H-pyridin-2-one;
and pharmaceutically acceptable salts, tautomers and stereoisomers thereof.

17. A method of treating cancer, comprising administering a therapeutically effective amount of a compound according to claim 1 to a patient in need thereof.

18. The method of claim 17, wherein said cancer is selected from triple negative breast cancer, pancreas cancer, leukemia, melanoma and lung cancer.

19. A method of treating diabetes, comprising administering a therapeutically effective amount of a compound according to claim 1 to a patient in need thereof.

20. The method of claim 19, wherein said diabetes is type II diabetes.

21. A method of treating a disease, comprising administering a therapeutically effective amount of a compound according to claim 1 to a patient in need thereof, said disease being selected from inflammatory diseases, neurodegenerative disorders, cardiovascular disorders and viral infections.

22. A pharmaceutical composition comprising a compound according to claim 1 and a pharmaceutically acceptable diluent, carrier and/or excipient.

23. A pharmaceutical composition, comprising a therapeutically effective amount of a compound according to claim 1, and another anticancer agent selected from alkylating agents, antimetabolites, anticancer camptothecin derivatives, plan-derived anticancer agents, antibiotics, enzymes, platinum coordination complexes, tyrosine kinase inhibitors, hormones, hormone antagonists, monoclonal antibodies, interferons, and biological response modifiers.

* * * * *

UNITED STATES PATENT AND TRADEMARK OFFICE
CERTIFICATE OF CORRECTION

| | | |
|---|---|---|
| PATENT NO. | : 11,077,113 B2 | Page 1 of 1 |
| APPLICATION NO. | : 15/999530 | |
| DATED | : August 3, 2021 | |
| INVENTOR(S) | : Jessica Martinsson et al. | |

It is certified that error appears in the above-identified patent and that said Letters Patent is hereby corrected as shown below:

On the Title Page

<u>PLEASE REPLACE (57) ABSTRACT WITH THE FOLLOWING:</u>
The invention provides novel 6-aryl or 6-heteroaryl 4-morpholin-4-yl-pyridine-2-one compounds of formula (I), pharmaceutical compositions containing such compounds, and methods for using such compounds in treatment of diseases including cancer, diabetes, inflammatory diseases, neurodegenerative disorders, cardiovascular disorders and viral infections;

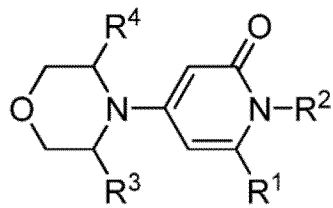

I wherein $R^1$, $R^2$, $R^3$ and $R^4$ are as defined in the specification.

Signed and Sealed this
Fifth Day of October, 2021

Drew Hirshfeld
*Performing the Functions and Duties of the
Under Secretary of Commerce for Intellectual Property and
Director of the United States Patent and Trademark Office*